United States Patent
Ueyama et al.

(10) Patent No.: US 9,886,808 B2
(45) Date of Patent: Feb. 6, 2018

(54) MAGNETIC PROPERTY DETERMINATION APPARATUS AND MAGNETIC PROPERTY DETERMINATION METHOD

(71) Applicant: GLORY LTD., Himeji-shi, Hyogo (JP)

(72) Inventors: Naoki Ueyama, Himeji (JP); Masaaki Hayashi, Himeji (JP)

(73) Assignee: GLORY LTD., Himeji-shi, Hyogo (JP)

( * ) Notice: Subject to any disclaimer, the term of this patent is extended or adjusted under 35 U.S.C. 154(b) by 136 days.

(21) Appl. No.: 14/778,337

(22) PCT Filed: Apr. 9, 2014

(86) PCT No.: PCT/JP2014/060300
§ 371 (c)(1),
(2) Date: Sep. 18, 2015

(87) PCT Pub. No.: WO2014/168180
PCT Pub. Date: Oct. 16, 2014

(65) Prior Publication Data
US 2016/0275744 A1   Sep. 22, 2016

(30) Foreign Application Priority Data
Apr. 9, 2013 (JP) .................. 2013-081488

(51) Int. Cl.
*G01N 27/72* (2006.01)
*G07D 7/04* (2016.01)
(Continued)

(52) U.S. Cl.
CPC .............. *G07D 7/04* (2013.01); *G01N 27/72* (2013.01); *G01N 27/84* (2013.01); *G01N 33/346* (2013.01);
(Continued)

(58) Field of Classification Search
CPC ....................................................... G01D 7/04
See application file for complete search history.

(56) References Cited

U.S. PATENT DOCUMENTS 5,418,458 A   5/1995  Jeffers
5,614,824 A   3/1997  Dames et al.
(Continued)

FOREIGN PATENT DOCUMENTS

JP   3-248895 A    11/1991
JP   H04-364498 A  12/1992
(Continued)

OTHER PUBLICATIONS

Russian Office Action (Non-English) (Application No. 2015141156/28(063469) (7 pages—dated Nov. 29, 2016).
(Continued)

*Primary Examiner* — Reena Aurora
(74) *Attorney, Agent, or Firm* — Renner, Kenner, Greive, Bobak, Taylor & Weber

(57) ABSTRACT

A magnetic property determination apparatus that detects a magnetic property of each magnetic material included in a paper sheet transported through a transport path and determines the magnetic materials. The magnetic property determination apparatus includes a magnetic detection unit that generates on the transport path a bias magnetic field having a magnetic field direction inclined to a transport surface of the paper sheet by a specific angle and detects the magnetic charge of the magnetic materials by detecting variation of the bias magnetic field; and a magnetization unit that is arranged upstream of the magnetic detection unit in the transport direction and magnetizes the magnetic materials by generating on the transport path a magnetization magnetic field having a magnetic field direction oriented in a direction different from the direction of the bias magnetic field. At a position at which the magnetic detection unit detects the
(Continued)

magnetism, the magnetic materials are in a state in which the magnetic materials are magnetized in mutually different magnetization directions according to coercive force thereof.

17 Claims, 17 Drawing Sheets

(51) Int. Cl.
| | |
|---|---|
| *G01N 27/84* | (2006.01) |
| *G01R 33/12* | (2006.01) |
| *G01R 33/09* | (2006.01) |
| *G06K 7/08* | (2006.01) |
| *G06K 19/06* | (2006.01) |
| *G01N 33/34* | (2006.01) |

(52) U.S. Cl.
CPC ........... *G01R 33/093* (2013.01); *G01R 33/12* (2013.01); *G06K 7/084* (2013.01); *G06K 19/06187* (2013.01); *G01R 33/09* (2013.01)

(56) References Cited

U.S. PATENT DOCUMENTS

| | | | |
|---|---|---|---|
| 9,595,152 B2 * | 3/2017 | Ueyama | ................. G01N 27/72 |
| 2009/0008922 A1 | 1/2009 | Schutzmann et al. | |
| 2010/0327062 A1 | 12/2010 | Lazzerini | |
| 2011/0233277 A1 | 9/2011 | Schutzmann et al. | |
| 2013/0119980 A1 | 5/2013 | Ogomi et al. | |

FOREIGN PATENT DOCUMENTS

| | | |
|---|---|---|
| JP | 6-180304 A | 6/1994 |
| JP | 6-180305 A | 6/1994 |
| JP | 11-53703 A | 2/1999 |
| WO | WO 2009/103352 A1 | 8/2009 |
| WO | WO 2010/052797 A1 | 5/2010 |

OTHER PUBLICATIONS

European Search Report (Application No. 14783293.5-PCT/JP2014/060300) (17 pages—dated Jan. 30, 2017).

* cited by examiner

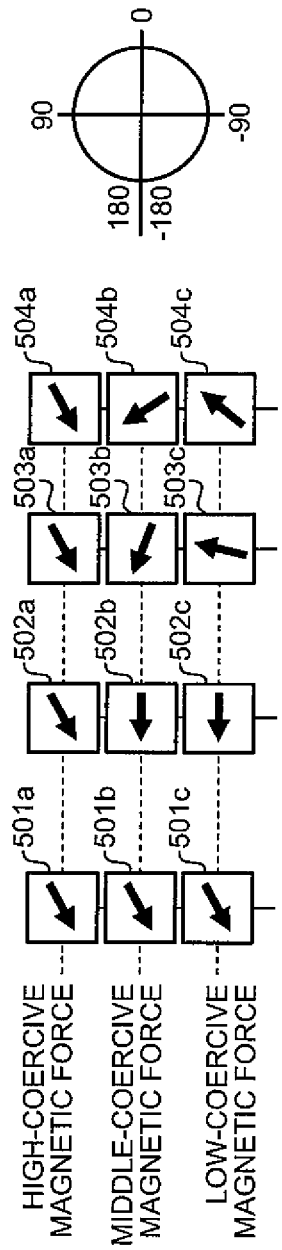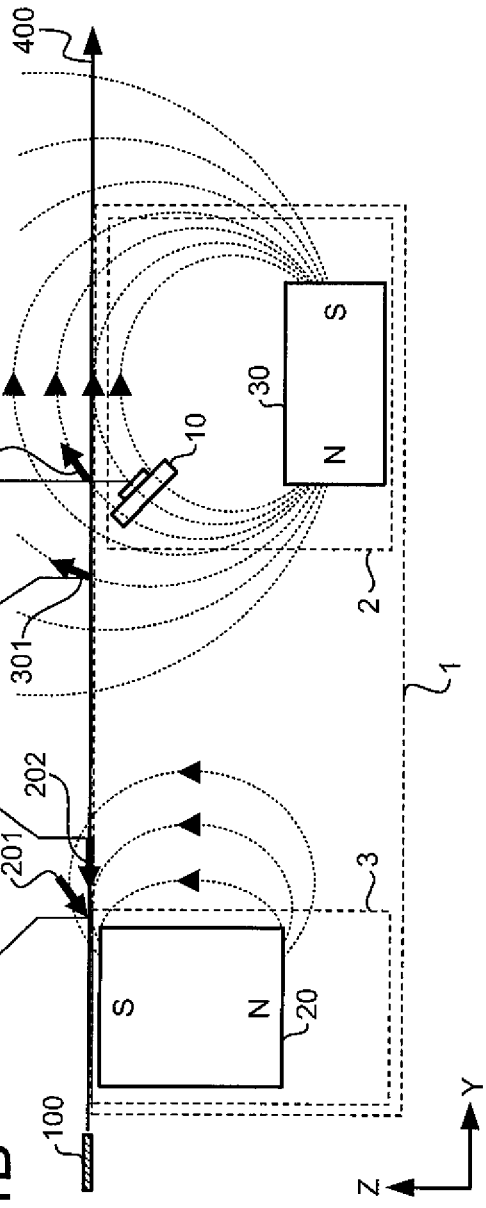

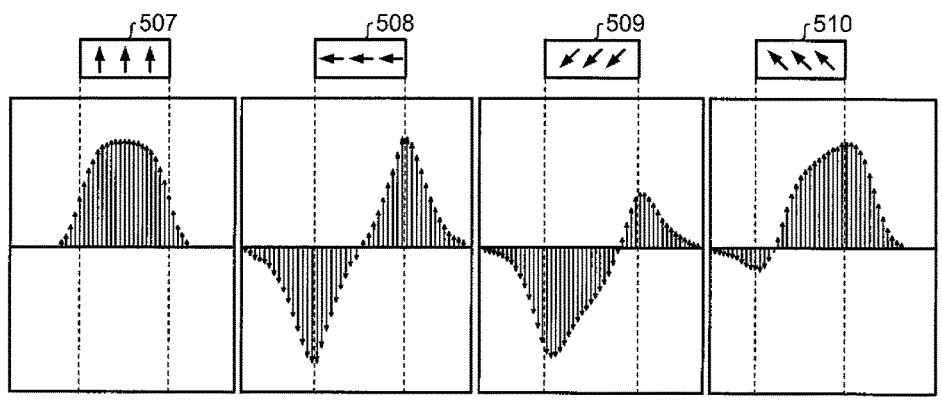

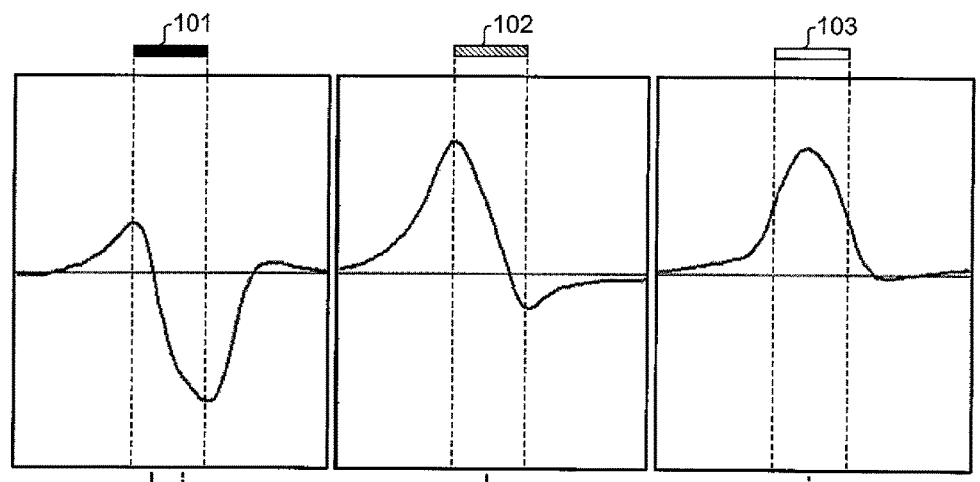
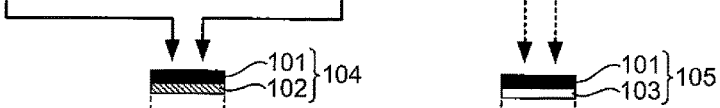
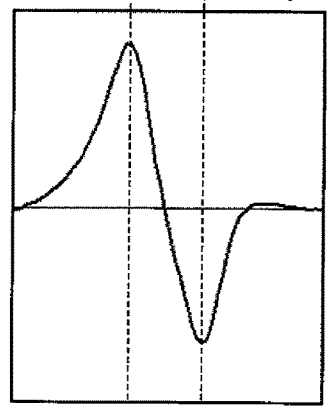
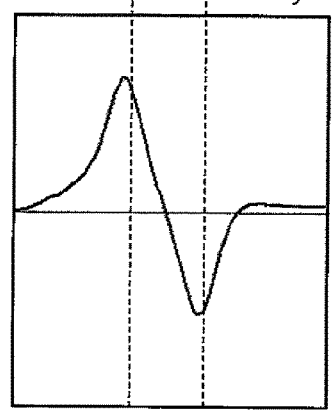
FIG.5A  FIG.5B  FIG.5C  FIG.5D  FIG.5E

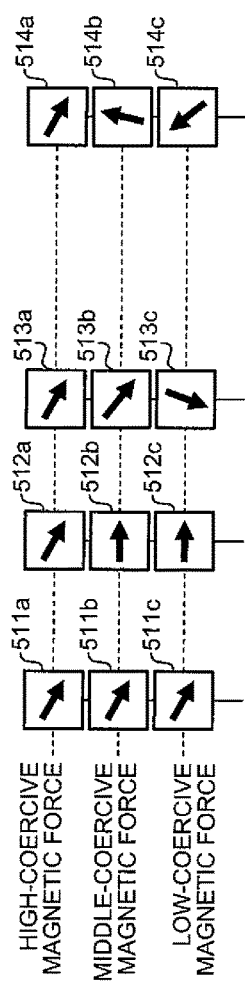
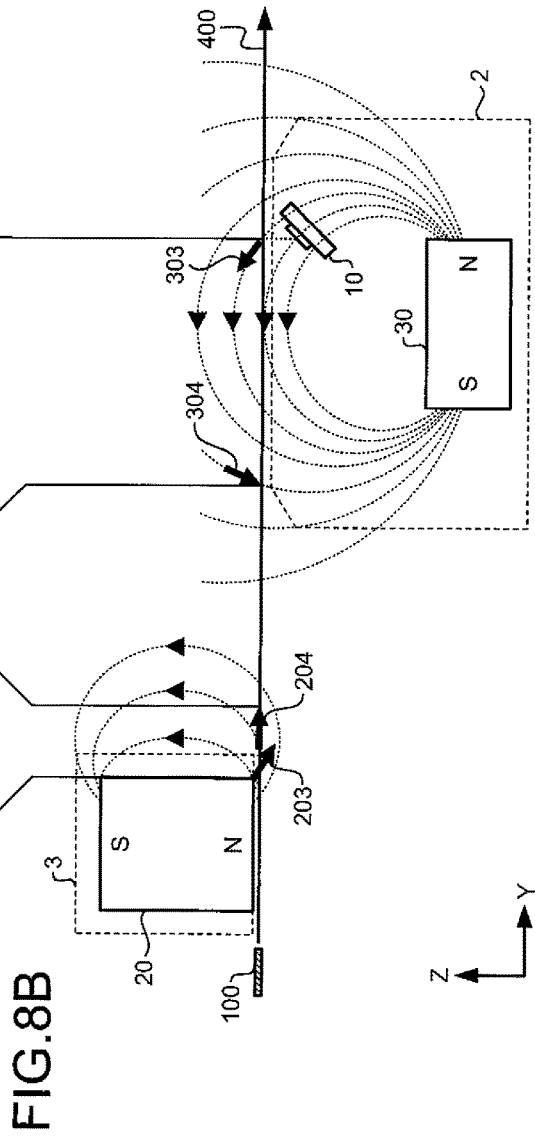

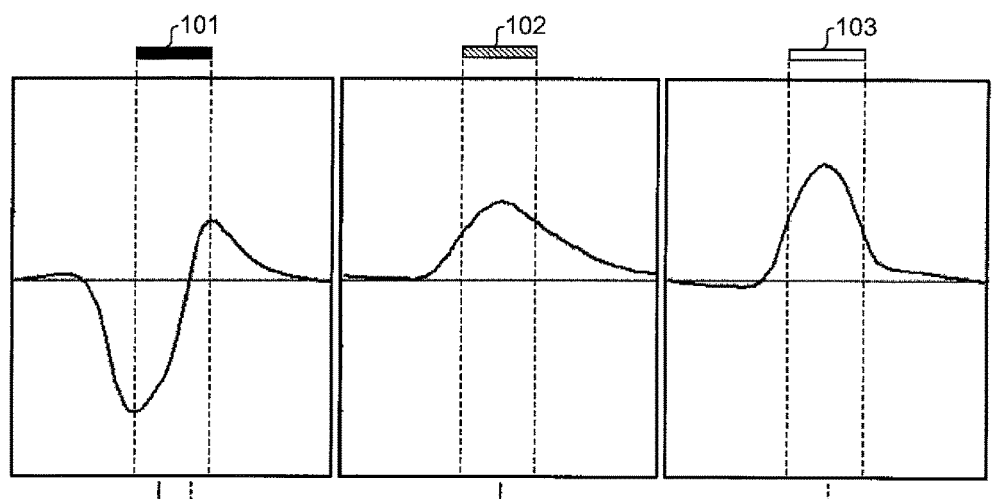
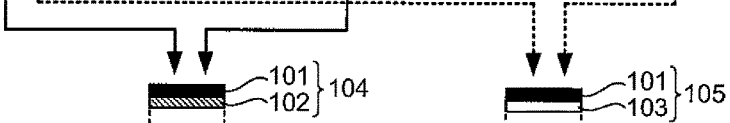
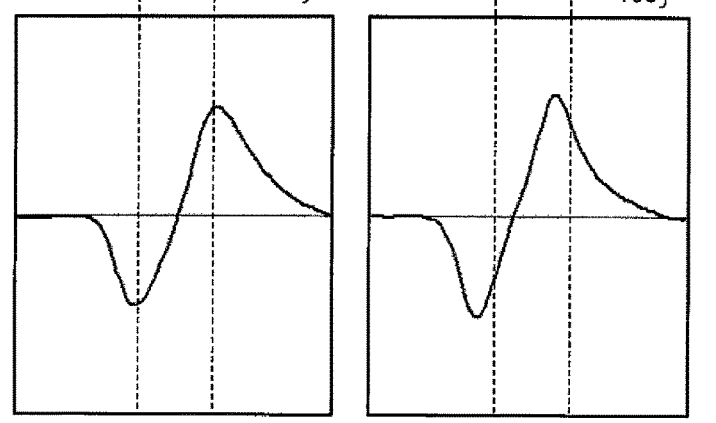
FIG.9A  FIG.9B  FIG.9C
FIG.9D  FIG.9E

FIG.11A 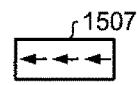 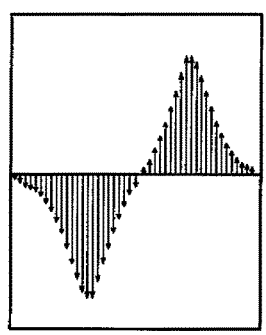
FIG.11B 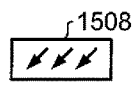 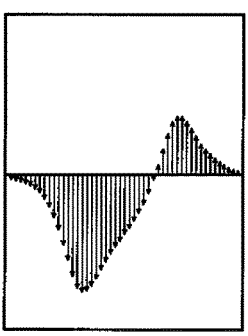
FIG.11C 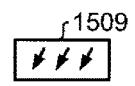 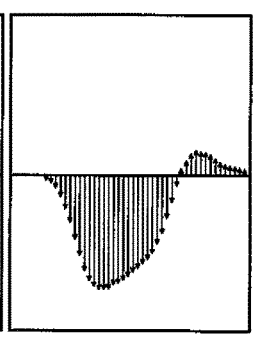
FIG.11D 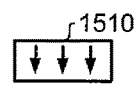 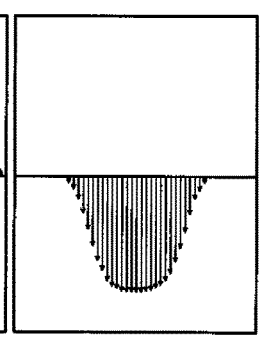
FIG.11E 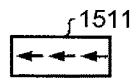 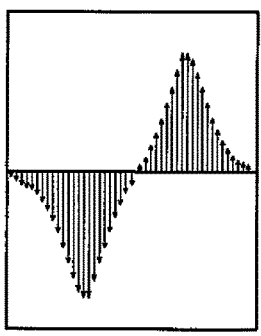
FIG.11F 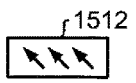 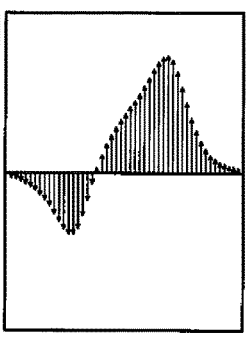
FIG.11G 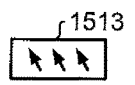 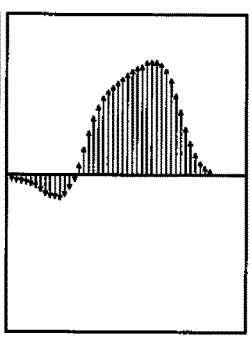
FIG.11H 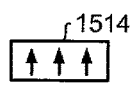 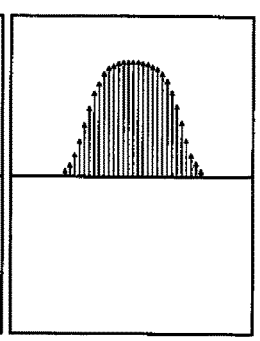

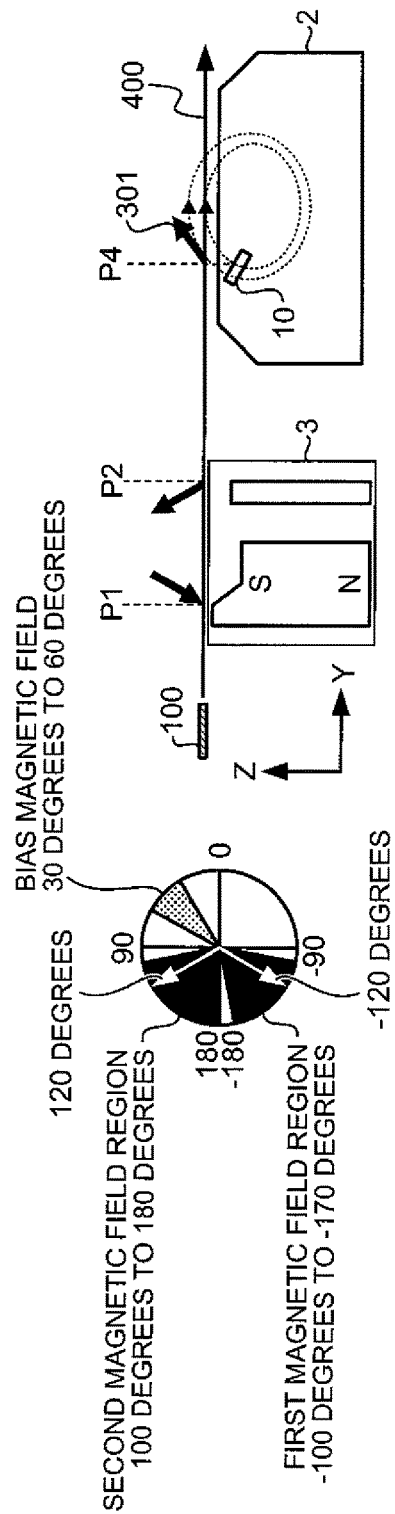

MAGNETIC PROPERTY DETERMINATION APPARATUS AND MAGNETIC PROPERTY DETERMINATION METHOD

TECHNICAL FIELD

The present invention generally relates to a magnetic property determination apparatus and a magnetic property determination method capable of detecting magnetism of a paper sheet. More specifically, the present invention specifically relates to a magnetic property determination apparatus and a magnetic property determination method capable of determining plural types of magnetic materials with different magnitudes of coercive force.

BACKGROUND ART

Conventionally, with an object to prevent forgery, magnetic ink including magnetic material has been used for printing on paper sheets such as checks, merchandise coupons, etc. Security techniques have been advancing year after year, and in recent years, there have been proposed paper sheets in which one paper sheet includes plural types of magnetic materials with different magnetic properties. For such paper sheets, it is necessary to determine each magnetic material included in the paper sheet to determine the authenticity of the paper sheet.

An example of an apparatus that determines plural types of magnetic materials included in a paper sheet has been disclosed in Patent Document 1. This document discloses an apparatus that determines magnetic materials with mutually different coercive forces. In this apparatus, a high-coercive force magnetic material and a low-coercive force magnetic material are magnetized in the same magnetization direction by a first magnet with a high magnetic force, and a detection signal corresponding to the magnetism of both the magnetic materials is obtained by using a first sensor. Subsequently, the magnetization direction of the low-coercive force magnetic material is changed by using a second magnet with a low magnetic force, and then a detection signal corresponding to the magnetism of the high-coercive force magnetic material only is obtained by using a second sensor. A difference between the detection signal obtained by the first sensor from both the high-coercive force magnetic material and the low-coercive force magnetic material and the detection signal obtained by the second sensor from only the high-coercive force magnetic material is taken as a detection signal obtained from only the low-coercive force magnetic material.

CITATION LIST

Patent Document

[Patent Document 1] U.S. Published Patent Application 2010/0327062

SUMMARY OF INVENTION

Technical Problem

However, in the conventional technique, because two magnets with a high magnetic force and a low magnetic force and two magnetic sensors are necessary, the number of parts increases, which leads to increase in the costs. Moreover, the overall structure becomes complicated and the size of the magnetic property determination apparatus increases.

The present invention has been devised to solve the problems explained above arising in the prior art. It is an object of the present invention to present a small-size magnetic property determination apparatus and a magnetic property determination method capable of determining plural types of magnetic materials with different magnitudes of coercive force.

Means for Solving Problems

To solve the above problems and to achieve the above objects, according to one aspect of the present invention, a magnetic property determination apparatus that detects a magnetic property of each magnetic material included in a paper sheet transported through a transport path and determines the magnetic materials includes a magnetic detection unit that generates on the transport path a bias magnetic field having a magnetic field direction inclined to a transport surface of the paper sheet by a specific angle and detects the magnetic charge of the magnetic materials by detecting variation of the bias magnetic field; and a magnetization unit that is arranged upstream of the magnetic detection unit in the transport direction and magnetizes the magnetic materials by generating on the transport path a magnetization magnetic field having a magnetic field direction oriented in a direction different from the direction of the bias magnetic field. At a position at which the magnetic detection unit detects the magnetism, the magnetic materials are in a state in which the magnetic materials are magnetized in mutually different magnetization directions according to coercive force thereof.

In the magnetic property determination apparatus according to the above aspect, magnetic field intensity of the magnetization magnetic field is set to magnetic field intensity for magnetizing a magnetic material having the highest coercive force among the magnetic materials that are the targets of determination into a saturation magnetization state, and the magnetic field intensity of the bias magnetic field is set to magnetic field intensity for magnetizing a low-coercive force magnetic material that is the target of determination into the saturation magnetization state and for not magnetizing other magnetic materials into the saturation magnetization state.

In the magnetic property determination apparatus according to the above aspect, the magnetic field intensity of the magnetization magnetic field is set to 1.5 times or more than the coercive force of the magnetic material having the highest coercive force among the magnetic materials that are the targets of determination, and the magnetic field intensity of the bias magnetic field is set to 2 times or less than the coercive force of a middle-coercive force magnetic material.

In the magnetic property determination apparatus according to the above aspect, when determining the low-coercive force magnetic material from other magnetic materials, the transport direction is taken as 0 degrees, and the direction of the bias magnetic field is set to a range between 30 degrees and 60 degrees or between 120 degrees and 150 degrees, and the direction of the magnetization magnetic field is set within a range excluding a range between 80 degrees and 100 degrees, or the direction of the bias magnetic field is set to a range between −30 degrees and −60 degrees or between −120 degrees and −150 degrees and the direction of the magnetization magnetic field is set within a range excluding a range between 80 degrees and 100 degrees.

In the magnetic property determination apparatus according to the above aspect, when performing determination among the low-coercive force magnetic material, the middle-coercive force magnetic material, and a high-coercive force magnetic material, and the transport direction is taken as 0 degrees, and a combination of the direction of the bias magnetic field and the direction of the magnetization magnetic field is set to any one of a range between 30 degrees and 60 degrees and between −100 degrees and −170 degrees, between 120 degrees and 150 degrees and between −10 degrees and −80 degrees, between −30 degrees and between −60 degrees and −100 and −170 degrees, and between −120 degrees and −150 degrees or between −10 degrees and −80 degrees.

In the magnetic property determination apparatus according to the above aspect, the magnetic detection unit determines the coercive force of a magnetic material based on the shape of a waveform of a detection signal obtained when the magnetic material is detected.

In the magnetic property determination apparatus according to the above aspect, if the waveform of the detection signal obtained when the magnetic material is detected is substantially symmetric in relation to a peak position, it is determined that the magnetic material is the low-coercive force magnetic material.

In the magnetic property determination apparatus according to the above aspect, if an output of a signal obtained when the low-coercive force magnetic material is detected is taken as a positive output, if the detection signal obtained when the magnetic material is detected has a positive peak value and a negative peak value and if a waveform of the detection signal is asymmetric in relation to a peak position, and if a ratio of the positive output is higher than a ratio of the positive output in the detection signal, then it is determined that the magnetic material is the middle-coercive force magnetic material, and if the ratio of the negative output is higher than the ratio of the positive output in the detection signal, then it is determined that the magnetic material is the high-coercive force magnetic material.

In the magnetic property determination apparatus according to the above aspect, if the detection signal obtained when the magnetic material is detected has a positive peak value and a negative peak value of a specific value or higher, and if the detection signal has a waveform obtained by adding the detection signal of the middle-coercive force magnetic material and the detection signal of the high-coercive force magnetic material, then it is determined that the magnetic material is a laminated magnetic material including the middle-coercive force magnetic material and the high-coercive force magnetic material or a laminated magnetic material including the low-coercive force magnetic material and the high-coercive force magnetic material.

According to another aspect of the present invention, a magnetic property determination apparatus that detects a magnetic property of each magnetic material included in a paper sheet transported through a transport path and determines the magnetic material includes a magnetic detection unit that generates on the transport path a bias magnetic field having a magnetic field direction inclined to a transport surface of the paper sheet by a specific angle and detects the magnetic charge of the magnetic materials by detecting variation of the bias magnetic field; and a magnetization unit that is arranged upstream of the magnetic detection unit in the transport direction and magnetizes the magnetic materials by generating on the transport path a magnetization magnetic field. The magnetization magnetic field includes a first magnetic field region on the transport path and a second magnetic field region on the transport path downstream of the first magnetic field region. Magnetic field intensity of the first magnetic field region is set to magnetic field intensity for magnetizing a high-coercive force magnetic material having the highest coercive force among the magnetic materials that are the targets of determination into a saturation magnetization state or to a state close to the saturation magnetization state, and magnetic field intensity of the second magnetic field region is set to magnetic field intensity for magnetizing a middle-coercive force magnetic material having a coercive force lower than that of the high-coercive force magnetic material into the saturation magnetization state or to a state close to the saturation magnetization state, and the magnetic field direction of the first magnetic field region and the magnetic field direction of the second magnetic field region are set to mutually different directions. At a position at which the magnetic detection unit detects the magnetism, the magnetic materials are in a state in which the magnetic materials are magnetized by the magnetization magnetic field and the bias magnetic field in mutually different magnetization directions according to the coercive force thereof.

In the magnetic property determination apparatus according to the above aspect, for the first the magnetic field region, the magnetic field direction is set within a range between −100 degrees and −170 degrees in relation to the transport direction that is taken as 0 degrees and the magnetic field intensity is set to 1.5 times or more than the coercive force of the high-coercive force magnetic material.

In the magnetic property determination apparatus according to the above aspect, for the second magnetic field region, the magnetic field direction is set within a range between 100 degrees and 180 degrees in relation to the transport direction that is taken as 0 degrees and the magnetic field intensity is set to 1.5 times or more than the coercive force of the middle-coercive force magnetic material and 1 time or less than the coercive force of the high-coercive force magnetic material.

In the magnetic property determination apparatus according to the above aspect, the magnetization unit includes a magnetization magnet and a magnetically conductive member arranged downstream of the magnetization magnet in the transport direction.

In the magnetic property determination apparatus according to the above aspect, the magnetization magnet includes one magnetic pole surface that is substantially parallel to a transport surface, which is arranged on a side of a top surface opposed to the transport path, and another magnetic pole surface that is more distant from the transport surface than the one magnetic pole surface, which is arranged downstream of the one magnetic pole surface in the transport direction.

In the magnetic property determination apparatus according to the above aspect, the magnetization magnet includes a chamfered region arranged downstream on the top surface opposed to the transport direction in the transport direction.

According to still another aspect of the present invention, a magnetic property determination method of detecting a magnetic property of each magnetic material included in a paper sheet transported through a transport path and determining the magnetic material includes generating on the transport path a bias magnetic field having a magnetic field direction inclined to a transport surface of the paper sheet by a specific angle and detecting the magnetic charge of the magnetic materials by detecting variation of the bias magnetic field; and magnetizing the magnetic material by generating on the transport path a magnetization magnetic field having a magnetic field direction oriented in a direction different from the direction of the bias magnetic field on an upstream side of a position at which the magnetic charge is detected at the detecting. When the magnetic charge is detected at the detecting, the magnetic materials are in a state in which the magnetic materials are magnetized by the magnetization magnetic field and the bias magnetic field in mutually different directions according to the coercive force thereof.

According to still another aspect of the present invention, a magnetic property determination method of detecting a magnetic property of each magnetic material included in a paper sheet transported through a transport path and determines the magnetic material includes generating on the transport path a bias magnetic field having a magnetic field direction inclined to a transport surface of the paper sheet by a specific angle and detecting the magnetic charge of the magnetic materials by detecting variation of the bias magnetic field; and magnetizing the magnetic material by generating on the transport path a magnetization magnetic field on an upstream side of a position at which the magnetic charge is detected at the detecting. The magnetization magnetic field includes a first magnetic field region on the transport path and a second magnetic field region on the transport path downstream of the first magnetic field region. Magnetic field intensity of the first magnetic field region is set to magnetic field intensity for magnetizing a high-coercive force magnetic material having the highest coercive force among magnetic materials that are the targets of determination into a saturation magnetization state or to a state close to the saturation magnetization state, and magnetic field intensity of the second magnetic field region is set to magnetic field intensity for magnetizing a middle-coercive force magnetic material having coercive force lower than that of the high-coercive force magnetic material into the saturation magnetization state or to a state close to the saturation magnetization state, and the magnetic field direction of the first magnetic field region and the magnetic field direction of the second magnetic field region are set to mutually different directions. When detecting the magnetic charge at the detecting, the magnetic materials are in a state in which the magnetic materials are magnetized by the magnetization magnetic field and the bias magnetic field in mutually different directions according to the coercive force thereof.

Advantageous Effects of Invention

According to the present invention, by using a magnetic charge detection type magnetic detection unit that generates a bias magnetic field in a magnetic field direction that is angled against a transport surface on which a paper sheet including a magnetic material is transported and detects the magnetism based on variation of the bias magnetic field, and a magnetization unit that magnetizes the magnetic material by using a magnetization magnetic field arranged on an upstream side in the transport direction and oriented in a direction different from the direction of the bias magnetic field, and in detecting magnetism by the magnetic detection unit, the magnetic materials have been magnetized in mutually different magnetization directions based on their coercive force, and thus the magnetic materials can be differentiated and determined based on detection waveforms that are different according to the coercive force of the respective magnetic material.

BRIEF DESCRIPTION OF DRAWINGS

FIGS. 1A and 1B are views that show a magnetic property determination method performed by a magnetic property determination apparatus according to a first embodiment.

FIGS. 3A, 3B, 3C and 3D are views shows magnetized state when magnetism is detected from a magnetic material.

FIGS. 5A, 5B, 5C, 5D and 5E are views show magnetic material detection signals obtained by the magnetic property determination apparatus.

FIGS. 8A and 8S are views that show a magnetic property determination method performed by a magnetic property determination apparatus that transports the paper sheet in the reverse direction.

FIGS. 9A, 9B, 9C, 9D and 9E are views that show a magnetism detection signal obtained by the magnetic property determination apparatus that transports the paper sheet in the reverse direction.

FIGS. 11A, 11B, 110, 11D, 11E, 11F, 11G and 11H are views that show magnetized states of a high-coercive force magnetic material and a middle-coercive force magnetic material when the magnetization direction of the magnetic materials have a specific angle.

FIG. 12 is a view that shows an example of a magnetic property determination apparatus according to the second embodiment where a magnetic field direction is different from a bias magnetic field direction.

FIGS. 16A, 16B, 160 and 16D are views that show another example of the shape of the side surface of the magnetization magnet.

DESCRIPTION OF EMBODIMENTS

Figure 2:
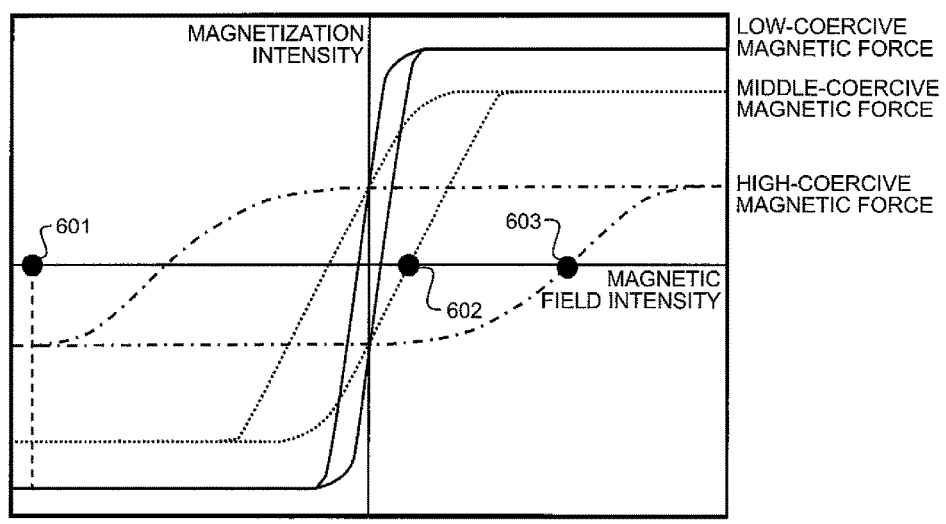
FIG. 2 is a view that shows magnetic field intensity of a magnetization magnetic field and a bias magnetic field.

Exemplary embodiments of a magnetic property determination apparatus and a magnetic property determination method according to the present invention are explained in detail below with reference to the accompanying drawings. The magnetic property determination apparatus according to the present embodiment detects magnetism of various magnetic materials used to perform printing on paper sheets such as checks, merchandise coupons, and valuable securities and determines the type of the magnetic material. The magnetic property determination apparatus is used in a paper sheet treatment apparatus to determine whether a paper sheet is authentic or not by determining the type of the magnetic material included in the paper sheet, for example.

The magnetic property determination apparatus according to the present embodiment is capable of determining which of a high-coercive force magnetic material, a middle-coercive force magnetic material, and a low-coercive force magnetic material the magnetic material is based on a detection signal obtained from the magnetic material. Magnetic materials that can be determined are a high-coercive force magnetic material, a middle-coercive force magnetic material, and a low-coercive force magnetic material in descending order of the coercive force. The terms "high-coercive force magnetic material", "middle-coercive force magnetic material", and "low-coercive force magnetic material" refer to magnetic materials in which the ratio of coercive force of the high-coercive force magnetic material to coercive force of the middle-coercive force magnetic material is 2 or more and the ratio of coercive force of the middle-coercive force magnetic material to coercive force of the low-coercive force magnetic material is 2 or more. However, it is preferable that this ratio of coercive force of the high-coercive force magnetic material to coercive force of the middle-coercive force magnetic material and coercive force of the middle-coercive force magnetic material to coercive force of the low-coercive force magnetic material is 10 or more. Specifically, in determination performed by a magnetic property determination apparatus 1, a magnetic material of coercive force of 50 Oe is determined as a low-coercive force magnetic material, a magnetic material of coercive force of 300 Oe is determined as a middle-coercive force magnetic material, and a magnetic material of coercive force of 3,000 Oe is determined as a high-coercive force magnetic material, for example. The respective magnetic materials of the above-mentioned magnitudes of coercive force will be referred to as a "low-coercive force magnetic material", a "middle-coercive force magnetic material", and a "high-coercive force magnetic material", respectively.

[First Embodiment]

FIG. 1 is a schematic diagram for explaining a magnetic property determination method performed by the magnetic property determination apparatus 1 according to the present embodiment. FIG. 1B shows an outline of the magnetic property determination apparatus 1 and FIG. 1A shows the magnetized states of 3 types of magnetic materials with mutually different coercive forces.

Referring to FIG. 1B, the magnetic property determination apparatus 1 includes a magnetization unit 3 that magnetizes a magnetic material included in a paper sheet 100 transported on an upper portion of the apparatus, and a magnetic detection unit 2 that detects magnetism of the magnetic material included in the paper sheet 100.

The paper sheet 100 is transported by a not-shown transport mechanism over a transport path in a direction of an arrow 400 shown in FIG. 1B. The magnetic property determination apparatus 1 is arranged below the transport path. In the magnetic property determination apparatus 1, the magnetization unit 3 is arranged upstream of the magnetic detection unit 2 in the direction of transport. The magnetic material included in the paper sheet 100 is magnetized when the paper sheet 100 passes above the magnetization unit 3. Subsequently, a signal is obtained from the magnetic material when the paper sheet 100 is further transported and passes on the magnetic detection unit 2. The type of the magnetic material is determined based on the obtained detection signal.

The magnetization unit 3 includes a magnetization magnet 20 that generates a magnetization magnetic field that is oriented in a direction shown in FIG. 1B by broken line arrows. The magnetization magnetic field has magnetic field intensity that can magnetize all the magnetic materials that are targets of determination into a saturation magnetization state. Specifically, in order to magnetize the high-coercive force magnetic material having the highest coercive force among the magnetic materials that are targets of determination into the saturation magnetization state, the magnetic field intensity of the magnetization magnetic field shall be 1.5 times or more than the coercive force of the high-coercive force magnetic material. However, in order to obtain a complete saturation magnetization state, it is preferable that the magnetic field intensity of the magnetization magnetic field is 3 times or more than the coercive force of the high-coercive force magnetic material.

At the time of detecting the magnetic material, if the magnetic materials with mutually different coercive forces can be magnetized in mutually different magnetization directions, it is not necessary to magnetize the high-coercive force magnetic material into a complete saturation magnetization state. That is, it is sufficient that the high-coercive force magnetic material is magnetized into a state that is close to the saturation magnetization state. This will be explained in more detail below.

The magnetic detection unit 2 includes a bias magnet 30 that generates a bias magnetic field and a magnetic sensor 10 that detects magnetic material passing through the bias magnetic field and outputs a signal representing detection of the magnetic material. The bias magnet 30 generates a bias magnetic field around it in a manner shown in FIG. 1B by broken line arrows. One characteristic feature of the magnetic detection unit 2 is that the magnetic sensor 10 is arranged in an inclined state so as to make an angle with respect to a transport surface (X-Y plane) on which the paper sheet 100 is transported. With this configuration, a detection signal that corresponds to the magnetic charge of the magnetic material is outputted from the magnetic sensor 10. In the present embodiment, an example in which the magnetic sensor 10 includes one magnetic detection element is explained; however, the magnetic sensor 10 can include two magnetic detection elements. The magnetic sensor 10 is operative to detect the amount of variation of the bias magnetic field that fluctuates in the vertical direction in FIG. 1B when magnetic material passes by. For example, a magneto-resistive element is used as the magnetic detection element, variation of the value of resistance of the magneto-resistive element is outputted as variation of the voltage value, and the voltage value is used as a detection signal obtained from the magnetic material. Details of the configuration, functions, and operations of the magnetic charge detection type magnetic detection unit 2 will be omitted herefrom because, for example, Japanese Patent No. 4894040 discloses such configuration, functions, and operations.

Similarly to the magnetic field intensity of the magnetization magnetic field, the magnetic field intensity of the bias magnetic field generated by the magnetic detection unit 2 is set according to the coercive force of the magnetic material that is the target of determination. FIG. 2 schematically shows saturation magnetization curves for the 3 types of magnetic materials that are targets of determination by the magnetic property determination apparatus 1, i.e., the low-coercive force magnetic material, the middle-coercive force magnetic material, and the high-coercive force magnetic material. The magnetic field intensity of the bias magnetic field is set to a magnitude between a coercive force 602 of middle-coercive force magnetic material and a coercive force 603 of high-coercive force magnetic material so that the low-coercive force magnetic material is magnetized into the saturation magnetization state while the middle-coercive force magnetic material is not magnetized into the saturation magnetization state. Specifically, the magnetic field intensity of the bias magnetic field is set, for example, 1.5 times of the coercive force 602 of middle-coercive force magnetic material. The magnetic field intensity of the magnetization magnetic field generated by the magnetization unit 3 corresponds to a point 601 shown in FIG. 2.

Next, a method for determining the magnetic materials including the high-coercive force magnetic material, the middle-coercive force magnetic material, and the low-coercive force magnetic material performed by the magnetic property determination apparatus 1 shown in FIG. 1B will be explained. In the following explanation, the direction of the magnetic field will be represented by using arrows and angles as shown in the drawing. With regard to the angles, as shown in the right portion of FIG. 1A, the positive side of the Y-axis, which is same as the transport direction 400, is taken as 0 degree, the positive side of the Z-axis, which extends above and orthogonal to the transport path, is taken as 90 degrees, and the negative side of the Y-axis, which extends opposite to the transport direction 400, is taken as 180 degrees. Similarly, the positive side of the Y-axis that is taken as 0 degree, the negative side of the Z-axis, which extends below and orthogonal to the transport path, is taken as −90 degrees, and the negative side of the Y-axis is taken as −180 degrees.

It is assumed that, for example, the magnetic field intensity of the magnetization magnetic field generated by the magnetization unit 3 shall be 1.5 times (4,500 G) of the coercive force of the high-coercive force magnetic material (3,000 Oe) at a position P1 on the transport path corresponding to an edge of the magnetization magnet 20 shown in FIG. 1B on the side of the south (S) pole thereof and on the side of the transport path. Moreover, for example, the magnetic field intensity of the bias magnetic field in the magnetic detection unit 2 is 1.5 times (450 G) than the coercive force (300 Oe) of the middle-coercive force magnetic material at a position P4 on the transport path at which the magnetism of the respective magnetic material is detected by the magnetic sensor 10.

At the position P4 at which the magnetism of the magnetic material is detected by the magnetic sensor 10, a direction 302 of the bias magnetic field is set between 30 degrees and 60 degrees. A direction 201 of the magnetization magnetic field at the position P1 is set based on the coercive force of the magnetic material that is the target of determination; however, if a high-coercive force magnetic material is the target of determination, the magnetic field direction 201 is set within a range between −100 degrees and −170 degrees. In the following description, it is assumed that the magnetic field direction at the position P1 is −160 degrees.

If the magnetic material included in the paper sheet 100 is the high-coercive force magnetic material (of 3,000 Oe), when the paper sheet 100 is transported on the magnetization unit 3 in the transport direction 400, the magnetic material is magnetized to the saturation magnetization state or to a state close to the saturation magnetization state when the magnetic material passes the position P1 shown in FIG. 1B because the magnetic field intensity of the magnetization magnetic field is very high (4,500 G). In this process, as shown in FIG. 1A, a magnetization direction 501a of the high-coercive force magnetic material is the same direction (about −160 degrees) as the direction 201 of the magnetization magnetic field at the position P1. The high-coercive force magnetic material attains the saturation magnetization state when its magnetization direction is between −150 degrees and −170 degrees.

As the paper sheet 100 passes the position P1 shown in FIG. 1B and is further transported in the transport direction 400, the intensity of the magnetization magnetic field steadily decreases, and thus the paper sheet 100 is not affected by the magnetization magnetic field. Accordingly, the magnetized state of the high-coercive force magnetic material does not change and a magnetization direction 502a of the high-coercive force magnetic material when the paper sheet 100 passes the position P2 remains to be in the same direction as that of the magnetization direction 501a at the magnetization position P1.

Even when the paper sheet 100 is further transported and enters the bias magnetic field, the paper sheet 100 is not influenced by the bias magnetic field, because, the intensity (450 G) of the bias magnetic field is ⅙ or less of the coercive force of the high-coercive force magnetic material (3,000 G). Accordingly, a magnetization direction 503a when the magnetic material passes the position P3 and a magnetization direction 504a when the magnetic material passes the position P4 also remain to be the same direction as that of the magnetization direction 501a (about −160 degrees) that is the magnetization direction at the time of the magnetization.

If the magnetic material included in the paper sheet 100 is the middle-coercive force magnetic material, as shown in FIG. 1B, similar to the case of the high-coercive force magnetic material, when the paper sheet 100 is transported on the magnetization unit 3 in the transport direction 400, the magnetic material is magnetized into the saturation magnetization state at the position P1. In this process, similar to the case of the high-coercive force magnetic material, a magnetization direction 501b of the middle-coercive force magnetic material is the same direction as the direction 201 of the magnetization magnetic field at the position P1. However, in the case of the middle-coercive force magnetic material, because the coercive force of the middle-coercive force magnetic material is lower than that of the high-coercive force magnetic material, the paper sheet 100 is continuously influenced by the magnetization magnetic field while the paper sheet 100 is transported in the transport direction 400, and thus its magnetization direction varies according to the direction of the magnetization magnetic field. When the paper sheet 100 passes the position P2, a magnetization direction 502b of the middle-coercive force magnetic material becomes the same direction as a direction 202 of the magnetization magnetic field (about 180 degrees). When the paper sheet 100 is further transported, the magnetic field intensity decreases while the direction of the magnetization magnetic field changes from the direction of 180 degrees to the direction of 170 degrees, and the action of magnetization of the middle-coercive force magnetic material is lost.

When the paper sheet 100 is further transported and enters the bias magnetic field, the paper sheet 100 is influenced by the bias magnetic field. At the position P3, the magnetization direction is shifted toward the same direction as the direction 301 of the bias magnetic field at the position P3 to a magnetization direction 503b that is a direction slightly rotated from the magnetization direction 502b at the position P2. Moreover, the magnetization direction is rotated toward the same direction as the bias magnetic field direction 302 at the position P4 to a magnetization direction 504b that is a direction slightly rotated from the magnetization direction 503b at the position P3. However, the intensity (450 G) of the bias magnetic field is lower than the magnetic field intensity for turning the coercive force of the middle-coercive force magnetic material into the saturation magnetization state (300 Oe). Accordingly, the final magnetization direction of the middle-coercive force magnetic material is the magnetization direction 504b, which is a direction between the magnetization direction 502b that is the magnetization direction when the paper sheet 100 exits the magnetization magnetic field (about 180 degrees) and the direction 302 of the bias magnetic field at the position P4 (between 30 degrees and 60 degrees). For example, the magnetization direction 504b of the middle-coercive force magnetic material at the position P4 is about 120 degrees.

If the magnetic material included in the paper sheet 100 is the low-coercive force magnetic material, similarly to the cases of other magnetic materials, when the paper sheet 100 is transported on the magnetization unit 3 in the transport direction 400, as shown in FIG. 1B, the magnetic material is magnetized into the saturation magnetization state at the magnetizing position 21. In this process, similarly to the cases of other magnetic materials, a magnetization direction 501c of the low-coercive force magnetic material is the same direction as the direction 201 of the magnetization magnetic field at the magnetizing position P1. However, the coercive force of the low-coercive force magnetic material is low. Accordingly, the paper sheet 100 is continuously influenced by the magnetization magnetic field while the paper sheet 100 is transported in the transport direction 400, and the magnetization direction varies according to the direction of the magnetization magnetic field. Accordingly, similarly to the case of the middle-coercive force magnetic material, a magnetization direction 502c when the paper sheet 100 passes the position P2 is the same direction as the direction 202 of the magnetization magnetic field (about 180 degrees).

When the paper sheet 100 is further transported and enters the bias magnetic field, the low-coercive force magnetic material is also influenced by the bias magnetic field. At the position P3, the magnetization direction 502c of the low-coercive force magnetic material is a magnetization direction 503c that is the same as the direction 301 of the bias magnetic field at the position P3. At the position P4 also, the magnetization direction of the low-coercive force magnetic material is a magnetization direction 504c that is the same magnetization direction as the direction 302 of the bias magnetic field. Because the magnetic field intensity of the bias magnetic field (450 G) is sufficiently higher than the coercive force of the low-coercive force magnetic material (50 Oe) and the low-coercive force magnetic material turns into the saturation magnetization state at the respective positions, the magnetization direction of the low-coercive force magnetic material at the each of the above-mentioned positions is the direction that is the same as the direction of the bias magnetic field at those positions.

It is said that the magnetic field intensity that is 3 times higher than the coercive force is required to turn the magnetic material into the saturation magnetization state. Accordingly, in the magnetic property determination apparatus 1, the intensity of the bias magnetic field at the position P4 at which magnetism is detected by the magnetic sensor 10 is set 3 times or more than the low-coercive force magnetic material that is the target of determination and 2 times or less than the coercive force of the middle-coercive force magnetic material. However, this does not apply around the magnetic field with the magnetic field intensity equivalent to the coercive force of the middle-coercive force magnetic material. The reason is because the output of the magnetic material of the middle-coercive force magnetic material becomes 0 in the bias magnetic field. For example, the magnetic field intensity is set to 450 Oe so that the middle-coercive force magnetic material of the coercive force of 300 Oe would not be magnetized into the saturation magnetization state but the low-coercive force magnetic material of the coercive force of 50 Oe is turned into the saturation magnetization state. The magnetization direction 504c at the position P4 of the low-coercive force magnetic material can be thereby set to the same direction as the bias magnetic field direction 302 at the position P4. On the contrary, the magnetization magnetic field is set so that the magnetization direction of the middle-coercive force magnetic material varies in the bias magnetic field but it would be oriented in a direction that is not the same as the bias magnetic field direction 302 after the magnetization direction of the middle-coercive force magnetic material has varied. Accordingly, the magnetization direction 504b of the middle-coercive force magnetic material at the position P4 and the magnetization direction 504c of the low-coercive force magnetic material can be set to be mutually different.

In the case of the high-coercive force magnetic material, the magnetization direction remains to be in the magnetization direction 501a that is the same direction as the direction 201 of the magnetization magnetic field without being influenced by the bias magnetic field. However, because the direction 201 of the magnetization magnetic field has been set so as to be different from the magnetization direction 504b of the middle-coercive force magnetic material at the position P4 and the magnetization direction 504c of the low-coercive force magnetic material at the position P4, the magnetization direction 504a of the high-coercive force magnetic material at the position P4 can be set to a direction different from the magnetization directions 504b and 504c of other magnetic materials. If the magnetization direction 504a of the high-coercive force magnetic material can be set to a direction different from the magnetization directions 504b and 504c of the middle-coercive force magnetic material and the low-coercive force magnetic material, it is not necessary to magnetize the high-coercive force magnetic material into the saturation magnetization state, and it is allowable that the high-coercive force magnetic material is magnetized into a state close to the saturation magnetization state.

As explained above, one of the characteristics of the present invention is that, in the magnetic property determination apparatus 1, at the position P4 where the magnetic detection unit 2 detects the magnetization in the transport path, all of the magnetization direction 504a of high-coercive force magnetic material, the magnetization direction 504b of the middle-coercive force magnetic material, and the magnetization direction 504c of the low-coercive force magnetic material are oriented in different directions.

In the magnetic property determination apparatus 1 shown in FIG. 1, the magnetic field intensity of the magnetization magnetic field generated by the magnetization unit 3 is set to the magnetic field intensity with which the high-coercive force magnetic material can be magnetized into the saturation magnetization state and the magnetic field intensity of the bias magnetic field is set to the magnetic field intensity that does not influence the magnetized state of the high-coercive force magnetic material. Moreover, the direction 201 of the magnetization magnetic field at the position P1 at which the high-coercive force magnetic material is magnetized into the saturation magnetization state and the direction 302 of the bias magnetic field at the position P4 at which the magnetic material is detected are set so as to fall in the quadrants that are mutually opposite with respect to the origin. Furthermore, the intensity of the bias magnetic field at the position P4 is set to intensity for magnetizing the low-coercive force magnetic material into the saturation magnetization state and not magnetizing the middle-coercive force magnetic material into the saturation magnetization state. By performing the setting in the above-explained manner, at the position P4, the magnetization direction 504a of the high-coercive force magnetic material can be set to the same direction as the direction 201 of the magnetization magnetic field, the magnetization direction 504c of the low-coercive force magnetic material can be set to the same direction as the direction 302 of the bias magnetic field, and the magnetization direction 504b of the middle-coercive force magnetic material can be set to a direction between the magnetization direction 504a of the high-coercive force magnetic material and the magnetization direction 504c of the low-coercive force magnetic material. If the magnetization directions and the magnetic field intensities of the magnetization magnetic fields explained above can be achieved, the type, the number, the shape, and the like of the magnetization magnet 20 of the magnetization unit 3 are not particularly limited.

Next, detection signals acquired when the high-coercive force magnetic material, the middle-coercive force magnetic material, and the low-coercive force magnetic material having been magnetized into the magnetization directions different from one another as explained above are detected by the magnetic sensor 10 of the magnetic detection unit 2 will be explained.

FIG. 3 shows magnetic field distributions in the Z-axis direction at locations close to a location immediately below the magnetic material having been magnetized into magnetization directions 507 to 510 (at a location about 0.5 mm below the magnetic material). The magnetic field distribution in the Z-axis direction is shown in FIG. 3A when the magnetization direction is in the upward magnetization direction 507. The magnetic field distribution in the Z-axis direction is shown in FIG. 3B when the magnetization direction is in a leftward direction 508. The magnetic field distributions in the Z-axis direction are shown in FIG. 3C and FIG. 3D when the magnetization directions are inclined directions 509 and 510. When a magnetic material that has been magnetized passes through the bias magnetic field generated by the bias magnet 30, the direction and the density of the bias magnetic field vary as shown in FIG. 3. The magnetic sensor 10 outputs the variation of the bias magnetic field as a detection signal. The leftward direction in FIG. 3 corresponds to the direction of 180 degrees in FIG. 1 and the upward direction in FIG. 3 corresponds to the direction of 90 degrees in FIG. 1.

Figure 4A:
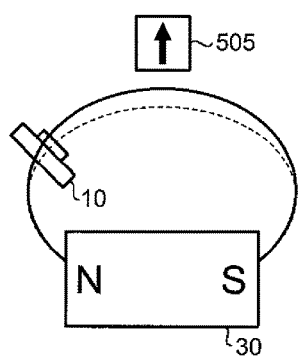
FIGS. 4A and 4B are views show a relationship between the magnetized state and the detection signal obtained by a magnetic sensor.
Figure 4B:
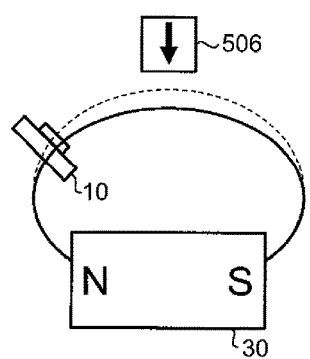

FIG. 4A and FIG. 4B are views that show a relationship between variation of the bias magnetic field and the detection signal from the magnetic sensor 10. In FIG. 4A and FIG. 4B, the magnetization direction of the magnetic material that passes through the bias magnetic field is shown in the upper portion, and the variation of the magnetic lines of force of the bias magnetic field is illustrated in the lower portion. As shown in FIG. 4A, when a magnetic material with a magnetization direction 505 passes the position P4 at which the magnetic sensor 10 detects the magnetic material, the magnetic lines of force shift upwardly as indicated by a solid line from an initial state indicated by a broken line. A setting has been performed so that a positive output detection signal can be obtained at the magnetic sensor 10 in response to the variation of the direction of the bias magnetic field and the variation of the magnetic flux density thereof. On the contrary, as shown in FIG. 4B, when the magnetic material with a magnetization direction 506 passes the position P4 at which the magnetic sensor 10 detects the magnetic material, the magnetic lines of force shift downwardly as indicated by a solid line from an initial state indicated by a broken line. In this case, a setting has been performed so that a negative output detection signal can be obtained at the magnetic sensor 10 in response to the variation of the direction of the bias magnetic field and the variation of the magnetic flux density thereof.

FIG. 5A to FIG. 5E show waveforms of the detection signals acquired when the magnetic detection unit 2 detects a high-coercive force magnetic material 101, a middle-coercive force magnetic material 102, a low-coercive force magnetic material 103, and laminated magnetic materials 104 and 105. Outputs from the magnetic sensor 10 are taken on the ordinate axis and time is taken on the abscissa axis. When the paper sheet 100, which includes the respective magnetic material, passes the position P4, the detection signals outputted from the magnetic sensor 10 has the waveforms shown in FIG. 5A to FIG. 5E. The respective magnetic materials 101 to 105 corresponding to the respective detection signals are shown in the upper portions of FIG. 5A to FIG. 5E.

In the case of the low-coercive force magnetic material 103 shown in FIG. 5C, a positive output is obtained in substantially the entire range, and the waveform is substantially symmetrical across the peak position. Because the low-coercive force magnetic material 103 is in a state in which it is saturation-magnetized by the bias magnetic field, the waveform of the detection signal output from the magnetic sensor 10 is not a waveform generated by the magnetic field generated by the low-coercive force magnetic material. Because the low-coercive force magnetic material has a high magnetic permeability and acts to converge the magnetic lines of force, the amplitude of the detection signal outputted from the magnetic sensor 10 increases as the low-coercive force magnetic material comes close to the position P4. Accordingly, the detection signal obtained when the low-coercive force magnetic material is detected has a maximum value when the magnetic material passes a location near the position P4 and takes substantially symmetrical waveform across the maximum value. For the middle-coercive force magnetic material and the high-coercive force magnetic material, the generated magnetic field is asymmetric for the magnetic field other than the upward direction (between 80 degrees and 100 degrees), and thus the detection signal necessarily becomes asymmetric across the maximum value.

FIG. 5B shows a detection signal obtained from the middle-coercive force magnetic material 102. At the position P4 in the magnetic property determination apparatus 1 shown in FIG. 1B, the magnetization direction of the middle-coercive force magnetic material is oriented in the upward left direction. The magnetic field distribution immediately below and near the middle-coercive force magnetic material in the Z-axis direction in this case is as shown in FIG. 3D, and a magnetic signal is detected so as to go along the shape of the magnetic field distribution from the right. As a result, as shown in FIG. 5B, the detection signal changes from a positive output to a negative output. As explained above, the portion of the detection signal having the positive output is larger for the middle-coercive force magnetic material 102. Similarly to the case of the low-coercive force magnetic material 103, the output of the detection signal of the middle-coercive force magnetic material 102 is positive for the substantially entire range; however, because the waveform of a positive output is asymmetric across the peak position, the detection signal of the middle-coercive force magnetic material 102 can be differentiated from the detection signal of the low-coercive force magnetic material 103.

FIG. 5A shows a detection signal obtained from the high-coercive force magnetic material 101. At the position P4 in the magnetic property determination apparatus 1 shown in FIG. 1B, the magnetization direction of the high-coercive force magnetic material is oriented in the downward left direction. The magnetic field distribution at a position close to a position immediately below the high-coercive force magnetic material in the Z-axis direction at this timing is as shown in FIG. 3C, and a magnetic signal is detected so as to go along the shape of the magnetic field distribution from the right. As a result, as shown in FIG. 5A, the detection signal changes from a positive output to a negative output. In the case of the high-coercive force magnetic material 101, the positive output takes an asymmetric waveform similar to the case of the middle-coercive force magnetic material 102; however, because the portion of the negative output is higher compared with the detection signal of the middle-coercive force magnetic material 102 shown in FIG. 5B, the detection signal of the high-coercive force magnetic material 101 can be differentiated from the detection signal of the low-coercive force magnetic material 103 and the detection signal of the middle-coercive force magnetic material 102.

For the laminated magnetic material 104 shown in FIG. 5D and constituted by the high-coercive force magnetic material 101 and the middle-coercive force magnetic material 102, the detection signal changes from a positive output to a negative output. The waveform of the detection signal obtained from of the laminated magnetic material 104 is obtained by adding the detection signal of the high-coercive force magnetic material 101 and the detection signal of the middle-coercive force magnetic material 102. The detection signal obtained from the laminated magnetic material 104 has both positive and negative outputs similarly to the high-coercive force magnetic material 101 shown in FIG. 5A. However, differently from the detection signal of the high-coercive force magnetic material 101, the amplitude is substantially the same for the positive output and the negative output in the detection signal of the laminated magnetic material 104, and thus the detection signal of the laminated magnetic material 104 and the detection signal of the high-coercive force magnetic material 101 can be differentiated from each other. If only one type of laminated magnetic material is included in the magnetic material that is the target of determination and the laminated magnetic material is the laminated magnetic material 104 including the high-coercive force magnetic material 101 and the middle-coercive force magnetic material 102, it can be recognized by using the above-explained determination method that the laminated magnetic material 104 exists at a specific location on the paper sheet 100.

In case of the laminated magnetic material 105 shown in FIG. 5E constituted by the high-coercive force magnetic material 101 and the low-coercive force magnetic material 103, the detection signal changes from a positive output to a negative output. The waveform of the detection signal obtained from the laminated magnetic material 105 is obtained by adding the detection signal of the high-coercive force magnetic material 101 and the detection signal of the low-coercive force magnetic material 103. The detection signal of the laminated magnetic material 105 has both positive and negative outputs similarly to the detection signal obtained from the high-coercive force magnetic material 101 shown in FIG. 5A. However, differently from the detection signal obtained from the high-coercive force magnetic material 101, the amplitude is substantially the same for the positive output and the negative output in the detection signal obtained from the laminated magnetic material 105. Accordingly, the detection signal obtained from the laminated magnetic material 105 and the detection signal obtained from the high-coercive force magnetic material 101 can be differentiated from each other. If only one type of laminated magnetic material is included in the target object of determination and the laminated magnetic material is the laminated magnetic material 105 including the high-coercive force magnetic material 101 and the low-coercive force magnetic material 103, it can be recognized by using the above-explained determination method that the laminated magnetic material 105 exists at a specific location on the paper sheet 100.

In the method of determining the laminated magnetic material, except for a case in which both of a combination of the high-coercive force magnetic material 101 and the middle-coercive force magnetic material 102 and a combination of the high-coercive force magnetic material 101 and the low-coercive force magnetic material 103 coexist on one paper sheet 100, it is possible to determine whether a detection signal obtained from a laminated magnetic material has been obtained from the laminated magnetic material 104 including the high-coercive force magnetic material 101 and the middle-coercive force magnetic material 102, or has been obtained from the laminated magnetic material 105 including the high-coercive force magnetic material 101 and the low-coercive force magnetic material 103.

The detection signals obtained from the laminated magnetic materials shown in FIG. 5D and FIG. 5E were explained by taking examples in which the high-coercive force magnetic material 101 existed in the upper layer. However, similar to these examples, the same applies to detection signals obtained from laminated magnetic materials in which the high-coercive force magnetic material 101 exists in the lower layer. In other words, a positional relationship between the laminates does not influence the determination.

As shown in FIG. 5, in order to obtain detection signals having a waveform that can differentiate among the high-coercive force magnetic material 101, the middle-coercive force magnetic material 102, the low-coercive force magnetic material 103, and the laminated magnetic material (104 and 105), for example, the direction 201 of the magnetization magnetic field is set at about −160 degrees on an edge of the magnetization magnet 20 and the direction 302 of the bias magnetic field at the position P4 corresponding to the magnetic sensor 10 is set between 30 degrees and 60 degrees.

Figure 6A:
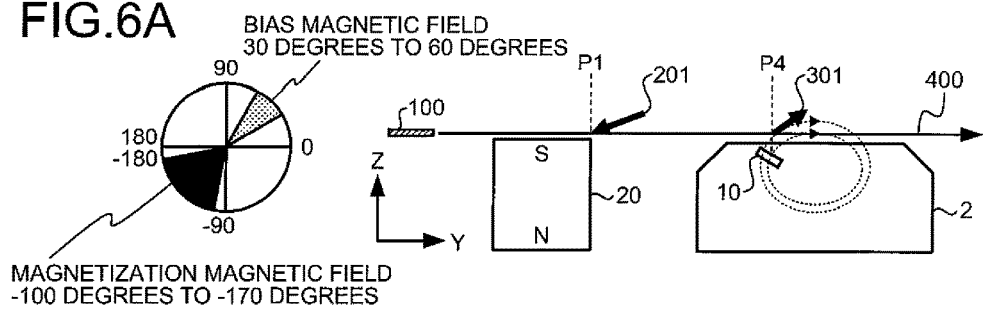
FIGS. 6A, 6B, 6C and 6D are views that show magnetic property determination apparatuses with a direction of a magnetic field being different from a direction of bias magnetic field.
Figure 6B:
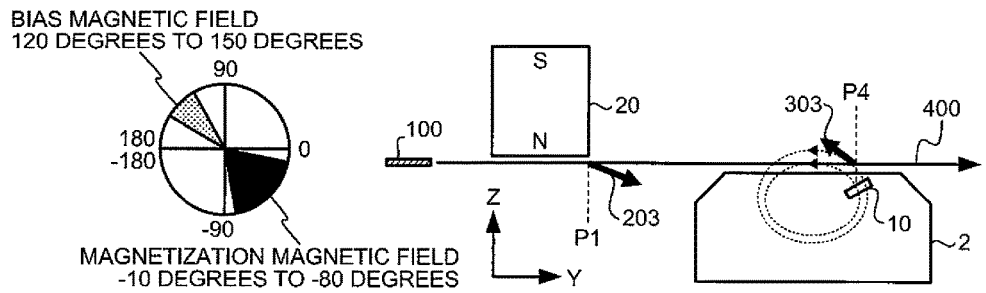
Figure 6C:
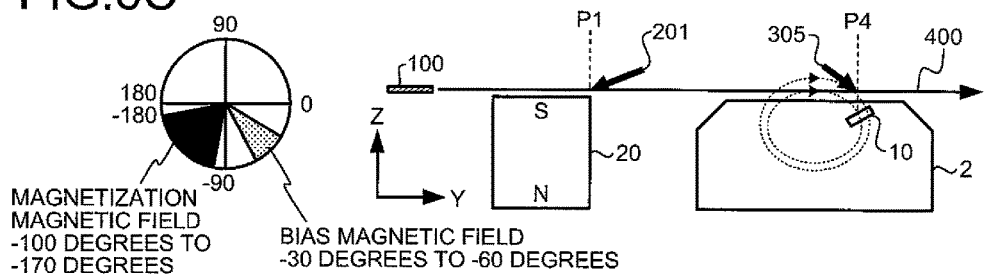
Figure 6D:
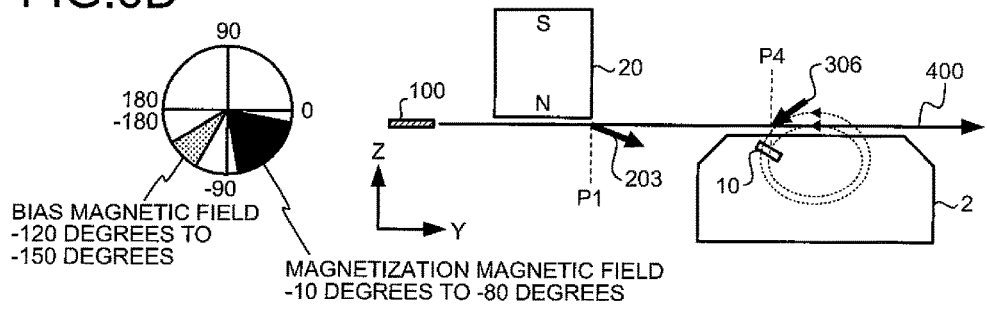

However, the relationship among the direction 201 of the magnetization magnetic field at the magnetizing the position P1, the direction 302 of the bias magnetic field at the position P4 where magnetism is detected, and the transport direction 400 is not limited to the relationship shown in FIG. 1. FIG. 6A to FIG. 6D are views that show the magnetic property determination apparatuses 1 with differently oriented magnetization magnetic fields, differently oriented bias magnetic fields, and different transport directions. FIG. 6A and FIG. 6C show the relationship in examples in which the paper sheet 100 is transported in a forward direction, and FIG. 6B and FIG. 6D show a relationship in examples in which the paper sheet 100 is transported by reverse-direction transport. The term "forward-direction transport" herein denotes to transport in which the angle between the transport direction 400 and the directions 301 and 305 of the bias magnetic field is 90 degrees or less. The term "reverse-direction transport" denotes to transport in which the angle between the transport direction 400 and the directions 303 and 306 of the bias magnetic field is 90 degrees or more.

The forward-direction transport shown in FIG. 6A is an example corresponding to FIG. 1, in which the transport direction 400 is the direction of 0 degrees and the direction 301 of the bias magnetic field at the detection position P4 is between 30 degrees and 60 degrees. In the forward-direction transport, the direction 201 of the magnetization magnetic field is set between −100 degrees and −170 degrees as shown in the left portion of FIG. 6A.

The magnetic detection unit 2 for reverse-direction transport shown in FIG. 6B is in a state in which it is arranged by reversely turning the magnetic detection unit 2 for forward-direction transport shown in FIG. 6A around the Z-axis by 180 degrees. In the example of the reverse-direction transport shown in FIG. 6B, the direction 303 of the bias magnetic field obtained at the detection position P4 is a laterally reversed direction of the magnetic field direction 301 of the magnetic detection unit 2 for the forward-direction transport around the Z-axis, i.e., in the direction between 120 degrees and 150 degrees. Similarly, a direction 203 of the magnetization magnetic field at the position P1 at which magnetization is performed is also a laterally reversed direction of the magnetic field direction 201 for the forward-direction transport around the Z-axis, that is, between −10 degrees and −80 degrees. In order to realize the direction 203 of the magnetization magnetic field explained above, the magnetization magnet 20 included in the magnetization unit 3 is arranged above the transport path.

For the magnetic detection unit 2 for the forward-direction transport shown in FIG. 6C, the direction 201 of the magnetization magnetic field is the same as the direction of the magnetization magnetic field for the magnetic detection unit 2 shown in FIG. 6A (between −100 degrees and −170 degrees), but the direction 305 of the bias magnetic field is a vertically reversed direction of the direction 301 of the bias magnetic field of the magnetic detection unit 2 shown in FIG. 6A around the Y-axis, i.e., between −30 degrees and −60 degrees. For the magnetic detection unit 2 for reverse-direction transport shown in FIG. 6D, the direction 203 of the magnetization magnetic field is in the same direction as the magnetic detection unit 2 shown in FIG. 6B (between −10 and −80 degrees), but the direction 306 of the bias magnetic field is a vertically reversed direction of the direction 303 of the bias magnetic field of the magnetic detection unit 2 shown in FIG. 6B around the Y-axis, i.e., between −120 degrees and −150 degrees.

In this manner, by setting the combination of the direction of the bias magnetic field and the direction of the magnetization magnetic such as from 30 degrees to 60 degrees and from −100 degrees to −170 degrees shown in FIG. 6A, from 120 degrees to 150 degrees and from −10 degrees to −80 degrees shown in FIG. 6B, from −30 degrees to −60 degrees and from −100 degrees to −170 degrees shown in FIG. 6C, or from −120 degrees to −150 degrees and from −10 degrees to −80 degrees shown in FIG. 6D with the transport direction 400 set as 0 degrees, detection signals that can be differentiated among the high-coercive force magnetic material 101, the middle-coercive force magnetic material 102, the low-coercive force magnetic material 103, and the laminated magnetic material (104 or 105) can be obtained as shown in FIG. 5A to FIG. 5E.

In FIG. 6A to FIG. 6D, the high-coercive force magnetic material 101, the middle-coercive force magnetic material 102, and the low-coercive force magnetic material 103 are respectively determined; however, if it is sufficient to differentiate and determine the low-coercive force magnetic material 103 from other magnetic materials, the condition for the range of angles that can be set as the direction of the magnetization magnetic field can be moderated. FIG. 7A to FIG. 7D are views that show relationships between the direction of the magnetization magnetic field and the direction of the bias magnetic field when the magnetic property determination apparatus 1 shown in FIG. 6A to FIG. 60 differentiates and determines the low-coercive force magnetic material 103 from other magnetic materials, i.e., from the high-coercive force magnetic material 101, the middle-coercive force magnetic material 102, and the laminated magnetic material 104. FIG. 7A to FIG. 7D correspond to FIG. 6A to FIG. 6D, respectively.

Figure 7A:
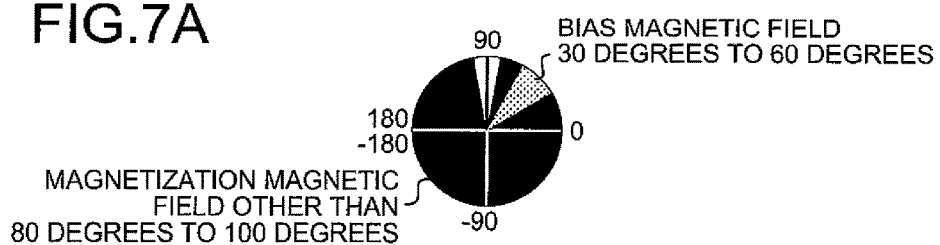
FIGS. 7A, 7B, 7C and 7D are views that show a direction of the magnetization magnetic field when a magnetic material to be determined by the magnetic property determination apparatus is different from one used in FIG. 6A to FIG. 6D.
Figure 7B:
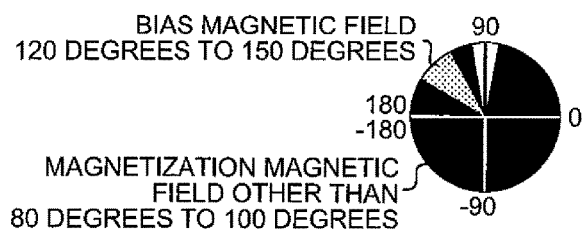
Figure 7C:
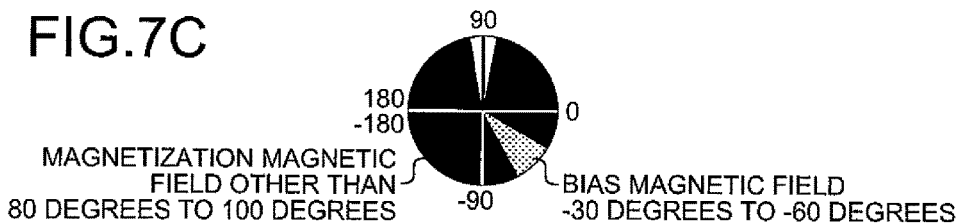
Figure 7D:
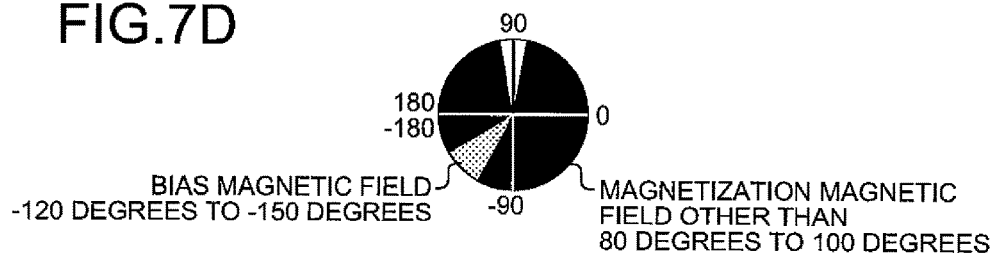

Specifically, when the magnetic property determination apparatus 1 of the forward-direction transport shown in FIG. 6A is required to differentiate and determine the low-coercive force magnetic material 103 from other magnetic materials, the direction of the magnetization magnetic field can be set to a direction other than between 80 degrees and 100 degrees as shown in FIG. 7A. Similarly, when the magnetic property determination apparatuses 1 shown in FIG. 6B to FIG. 6D are to differentiate and determine the low-coercive force magnetic material 103 from other magnetic materials, the direction of the magnetization magnetic field can be set to a direction other than between 80 degrees and 100 degrees as shown in FIG. 7B to FIG. 7D. By performing the setting in this manner, only positive output is obtained for the low-coercive force magnetic material 103 and a part of or all of the outputs of other magnetic materials are negative outputs as shown in FIG. 5, and thereby the magnetic materials can be determined.

Specifically, with the transport direction 400 set at 0 degrees, by setting the direction of the bias magnetic field between 30 degrees and 60 degrees (FIG. 7A) or between 120 degrees and 150 degrees (FIG. 7B) and by setting the direction of the magnetization magnetic field to an angle within a range excluding the angles between 80 degrees and 100 degrees, or by setting the direction of the bias magnetic field between −30 degrees and −60 degrees (FIG. 7D) or between −120 degrees and −150 degrees (FIG. 7D) and by setting the direction of the magnetization magnetic field to an angle within a range excluding the angles between 80 degrees and 100 degrees, the low-coercive force magnetic material 103 can be differentiated from other magnetic materials.

FIG. 8A and FIG. 8B are schematic diagrams that show the magnetic property determination method for examples of the reverse-direction transport shown in FIG. 6B. FIG. 8B shows an outline of the magnetic property determination apparatus 1, and FIG. 8A shows the magnetized states of 3 types of magnetic materials with mutually different coercive forces. For the apparatus configuration, the magnetic property determination apparatus 1 shown in FIG. 8B is different from the magnetic property determination apparatus 1 shown in FIG. 1 in a point such that in the magnetic property determination apparatus 1 shown in FIG. 8B the magnetization unit 3 including the magnetization magnet 20 is arranged above the transport path and in a point such that the magnetic detection unit 2 including the magnetic sensor 10 and the bias magnet 30 is arranged in a reversed manner around the Z-axis. In the magnetic property determination apparatus 1 shown in FIG. 8B, the direction 203 of the magnetization magnetic field and the direction 303 of the bias magnetic field are in a reversed direction of the directions 201 and 302 shown in FIG. 1B around the Z-axis.

If the magnetic material included in the paper sheet 100 is the high-coercive force magnetic material, when the paper sheet 100 is transported under (or on) the magnetization unit 3 in the transport direction 400, the high-coercive force magnetic material is magnetized into the saturation magnetization state or to a state close to the saturation magnetization state when the paper sheet 100 passes the magnetizing position P1 shown in FIG. 8B because the magnetic field intensity of the magnetization magnetic field is very high (4,500 G). In this process, as shown in FIG. 8A, a magnetization direction 511a of the high-coercive force magnetic material is the same direction as the direction 203 of the magnetization magnetic field at the magnetizing position P1 (about −20 degrees). Even when the paper sheet 100 is transported further in the transport direction 400, no such magnetic field exists that is intense enough to change the magnetized state of the high-coercive force magnetic material thereafter, and thus subsequent magnetization directions 512a, 513a, and 514a remain to be in the same direction as the magnetization direction 511a at the timing of the magnetization, i.e., the direction 203 of the magnetization magnetic field.

If the magnetic material included in the paper sheet 100 is the middle-coercive force magnetic material, the magnetic material is magnetized into the saturation magnetization state at the position P1. However, because the coercive force thereof is small compared with the high-coercive force magnetic material, the paper sheet 100 is continuously influenced by the magnetization magnetic field while the paper sheet 100 is transported in the transport direction 400, and thus a magnetization direction 512b at the position P2 and a magnetization direction 513b at the position P3 vary. Specifically, the magnetization direction 512b at the position P2 is the same as a magnetization direction 204 at the position P2, and the magnetization direction 513b at the position P3 is a direction between the magnetization direction 204 at the position P2 and the direction 304 of the bias magnetic field at the position P3. The final magnetization direction 514b is a direction between the magnetization direction 513b at the position P3 and a subsequent the direction 303 of the bias magnetic field at the detection position P4. In FIG. 8, although the magnetization intensity is not shown and only the magnetization directions are shown, the coercive force of the middle-coercive force magnetic material is reduced because the direction 303 of the bias magnetic field at the detection position P4 and the magnetization direction 513b at the position P3 are mutually opposite. As a result, as shown in FIG. 9B, the amplitude of the detection waveform of the middle-coercive force magnetic material is small.

If the magnetic material included in the paper sheet 100 is the low-coercive force magnetic material, because its coercive force is low, the magnetic material is continuously influenced by the magnetization magnetic field and the bias magnetic field while the paper sheet 100 is transported in the transport direction 400, and magnetization directions 511c to 514c at respective positions P1 to P4 are in the same directions as the magnetic field directions 203, 204, 304, 303 at the positions P1 to P4, respectively.

As explained above, also in the case of reverse-direction transport, similarly to the case of forward-direction transport shown in FIG. 1, all of the magnetization direction 514a of the high-coercive force magnetic material, the magnetization direction 514b of the middle-coercive force magnetic material, and the magnetization direction 514c of the low-coercive force magnetic material can be in mutually different directions at the detection position P4 at which the magnetic materials are detected. Accordingly, similarly to the detection signal in the case of the forward-direction transport shown in FIG. 5, detection signals having different waveforms can be obtained among the high-coercive force magnetic material 101, the middle-coercive force magnetic material 102, the low-coercive force magnetic material 103, and the laminated magnetic material (104 or 105).

FIG. 9A to FIG. 9E show waveforms of detection signals obtained when the high-coercive force magnetic material 101, the middle-coercive force magnetic material 102, the low-coercive force magnetic material 103, and the laminated magnetic material 104 or 105 are detected by the magnetic property determination apparatus 1 for reverse-direction transport shown in FIG. 8B. Outputs of the magnetic sensor 10 are taken on the ordinate axis, time is taken on the abscissa axis, and the waveforms shown in FIG. 9A to FIG. FIG. 9E are waveforms of the detection signals outputted from the magnetic sensor 10 when the paper sheet 100 including the respective magnetic materials passes the position P4. Similarly to the example shown in FIG. 5, the respective magnetic materials 101 to 105 corresponding to the detection signals are shown in the upper portion of FIG. 9A to FIG. 9E.

The waveform of the detection signal of the low-coercive force magnetic material 103 shown in FIG. 9C has a positive output for substantially the entire range also in the case of the reverse-direction transport similarly to the case of the forward-direction transport, and the waveform is substantially symmetric in relation to the peak position.

The output of the detection signal of the middle-coercive force magnetic material 102 shown in FIG. 9B is positive for substantially the entire range. The output of the detection signal is positive similarly to the low-coercive force magnetic material 103, and because the waveform thereof is symmetric in relation to the peak position, the detection signal can be differentiated from the detection signal of the low-coercive force magnetic material 103.

In the detection signal of the high-coercive force magnetic material 101 shown in FIG. 9A the output changes from a negative output to a positive output. The output of the detection signal is negative for almost the entire detection signal, and thus the detection signal can be differentiated from the detection signal of the low-coercive force magnetic material 103 and the detection signal of the middle-coercive force magnetic material 102.

In the laminated magnetic materials 104 and 105 shown in FIG. 9D and FIG. 9E the output changes from a negative output to a positive output. The waveform of the laminated magnetic material 104 shown in FIG. 9D is obtained by adding the detection signal of the high-coercive force magnetic material 101 and the detection signal of the middle-coercive force magnetic material 102. In contrast, in the laminated magnetic material 105 shown in FIG. 9E, the obtained waveform is a waveform by adding the detection signal of the high-coercive force magnetic material 101 and the detection signal of the low-coercive force magnetic material 103. In the laminated magnetic materials 104 and 105, both the positive and the negative outputs are obtained similarly to the high-coercive force magnetic material 101 shown in FIG. 9A. However, in the laminated magnetic material 104 and 105, the amplitude of the positive and the negative outputs are substantially the same which is different from the case of the detection signal of the high-coercive force magnetic material 101. Accordingly, the detection signal of the laminated magnetic materials 104 and 105 can be differentiated from the detection signal of the high-coercive force magnetic material 101.

In the forward-direction transport, the paper sheet 100 reaches the position P4, at which the magnetism is detected, immediately after entering the bias magnetic field. On the contrary, in the reverse-direction transport, the influence from the bias magnetic field on the middle-coercive force magnetic material 102 becomes high before the paper sheet 100 reaches the position P4. Specifically, the amount of magnetization on the middle-coercive force magnetic material 102 is reduced due to the influence from the bias magnetic field, and as can be understood from the comparison between FIG. 5B and FIG. 9B, the amplitude of the detection signal of the reverse-direction transport is smaller than the amplitude of the detection signal of the forward-direction transport. The high-coercive force magnetic material 101 is not influenced by the bias magnetic field because the magnetic field intensity of the bias magnetic field is smaller than the coercive force thereof.

As explained above, the waveforms of the detection signal of the magnetic material are different from each other between the forward-direction transport and the reverse-direction transport, however, in either cases, different detection signals are obtained from the high-coercive force magnetic material 101, the middle-coercive force magnetic material 102, the low-coercive force magnetic material 103, and the laminated magnetic materials 104 and 105. Accordingly, the respective magnetic materials 101 to 103 and the laminated magnetic materials 104 and 105 can be differentiated among them based on the detection signals.

The determination among the respective magnetic materials of the high-coercive force magnetic material 101, the middle-coercive force magnetic material 102, and the low-coercive force magnetic material 103 and the laminated magnetic material (104 or 105) based on the detection signal is performed by using the amplitude of the detection signal and the symmetry of the signal waveform in relation to the peak position. For example, if the amplitude at the peak position on the negative side is larger than a specific value, and if almost the entire detection signal is the negative output, then it is determined that the magnetic material is the high-coercive force magnetic material 101 based on the ratio between the time in which the negative output is obtained and the time in which the positive output is obtained. Otherwise, it is determined that the magnetic material is the laminated magnetic material 104. On the contrary, if the amplitude at the peak position on the negative side is smaller than a specific value, if the waveform on the positive side is substantially symmetric in relation to the peak position, then it is determined that the magnetic material is the low-coercive force magnetic material 103, and if the waveform on the positive side is substantially asymmetric in relation to the peak position, then it is determined that the magnetic material is the middle-coercive force magnetic material 102. The method for determining the symmetry of the signal waveform is not particularly limited, and the symmetry can be determined by comparing the distance from the peak position to a position at which the amplitude becomes 0 (zero) for the both directions, or the symmetry can be determined based on the correlation with the waveform obtained by reversing the original waveform in the lateral direction around the peak position as the axis.

According to the magnetic property determination apparatus 1 of the present embodiment, the high-coercive force magnetic material, the middle-coercive force magnetic material, the low-coercive force magnetic material, and the laminated magnetic material can be differentiated and determined from one another. Therefore, the type of the magnetic material included in the paper sheet 100 can be determined even if the magnetic material included in the paper sheet 100 is different according to the type of the paper sheet 100, and thus the authenticity of the paper sheet 100 can be determined. Moreover, if any pattern has been drawn on the paper sheet 100 by using the respective magnetic materials, the pattern can be recognized. Furthermore, if any code has been formed by a combination of the magnetic materials, the code can be recognized by correctly determining the respective magnetic materials.

As explained above, according to the present embodiment, the magnetic field intensity and the direction of the magnetization magnetic field generated by the magnetization unit 3 are appropriately set and the magnetic field intensity and the direction of the bias magnetic field by the magnetic detection unit 2 are appropriately set, and thereby the magnetization directions of the respective magnetic materials can be controlled to be different at the position at which the magnetism is detected by the magnetic detection unit 2. Accordingly, the respective magnetic materials can be differentiated and determined from one another based on the characteristic of the detection signal obtained when the magnetism is detected.

For example, the magnetic field intensity of the magnetization magnetic field is set to an intensity for magnetizing the high-coercive force magnetic material into the saturation magnetization state, the magnetic field intensity of the bias magnetic field is set to an intensity for magnetizing the low-coercive force magnetic material into the saturation magnetization state and for not magnetizing the middle-coercive force magnetic material into the saturation magnetization state. Moreover, the directions of the bias magnetic field at the position at which the magnetic material is detected by the magnetic detection unit 2 are set in mutually different directions. Accordingly, the high-coercive force magnetic material, the middle-coercive force magnetic material, the low-coercive force magnetic material, and the laminated magnetic material can be differentiated and determined from one another based on the amplitude and the waveform of the detection signal.

For example, the respective magnetic materials can be determined based on the detection signal obtained by one magnetic sensor 10 by realizing the above-explained magnetization magnetic field by using only one magnetization magnet 20. Therefore, thus reduction in the size and the cost of the magnetic property determination apparatus 1 can be achieved.

[Second Embodiment]

Figure 10A:
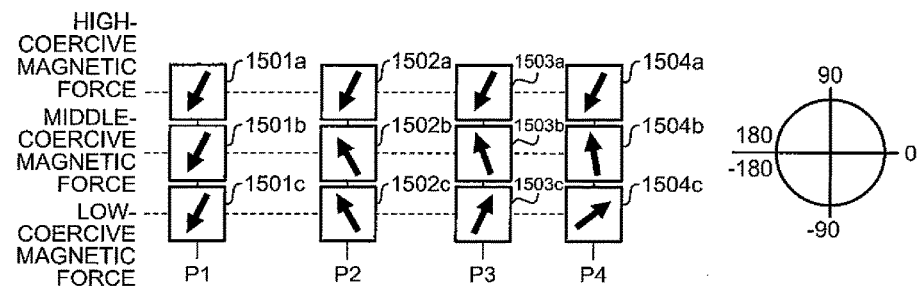
FIGS. 10A, 10B and 10C are views show a magnetic property determination method performed by a magnetic property determination apparatus according to a second embodiment.
Figure 10B:
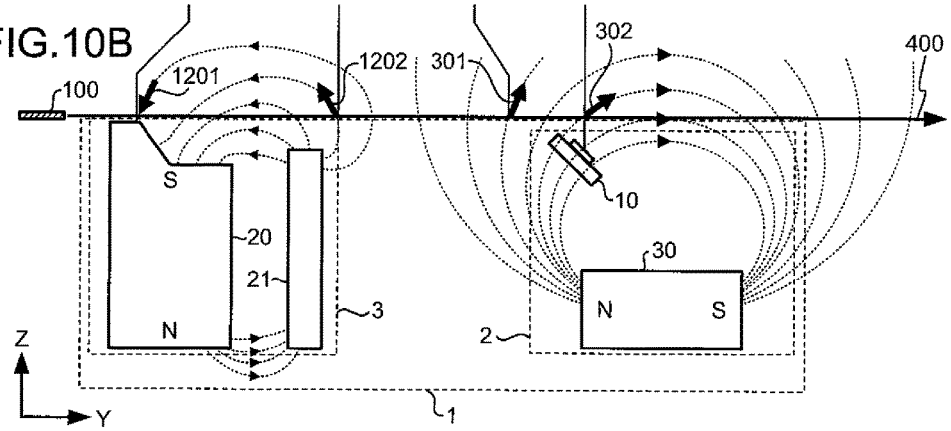
Figure 10C:
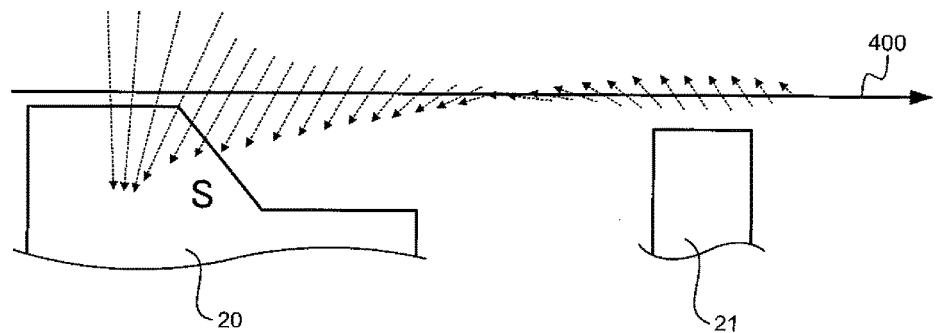

Next, another example of the magnetic property determination apparatus 1 that can detect magnetic materials with mutually different coercive forces based on the same principle as the first embodiment will be explained. FIG. 10A to FIG. 10C are schematic diagrams that show the magnetic property determination method performed by the magnetic property determination apparatus 1 according to the present embodiment. FIG. 10B shows the outline of the magnetic property determination apparatus 1, FIG. 10B shows the magnetized state of the 3 types of magnetic materials with different coercive forces, and FIG. 10C shows the magnetic field intensity and the direction of the magnetization magnetic field in the magnetization unit 3.

As shown in the drawing, the configuration in the present embodiment is different from that of the first embodiment in that the magnetization unit 3 includes the magnetization magnet 20 and a magnetically conductive member (yoke) 21. For example, materials with a high permeability such as iron plates and the like are used as the magnetically conductive member 21. In the following explanation, the configurations that are the same as those of the first embodiment will not be repeated and the exclusive characteristics of the present embodiment only will be explained.

Referring to FIG. 10B, the magnetic property determination apparatus 1 includes the magnetization unit 3 that magnetizes the magnetic material included in the paper sheet 100 transported on the apparatus, and the magnetic detection unit 2 that detects the magnetism of the magnetic material included in the paper sheet 100.

The magnetization unit 3 includes the magnetization magnet 20 and the magnetically conductive member 21. The magnetization magnet 20 is characteristic with respect to the shape of its side surface viewed from the side that is perpendicular to the transport direction 400 of the paper sheet 100. Specifically, the magnetization magnet 20 shown in FIG. 1 has a rectangular side surface shaped with a partially cut-off portion on the side of the top surface of the magnetization magnet 20 and on the downstream side in the transport direction (the upper right portion in the drawing). In addition, a first magnetic pole surface parallel to the transport surface (X-Y plane) and on the upstream side in the transport direction and a second magnetic pole surface parallel to the transport surface and on the downstream side in the transport direction are connected with each other via a sloped surface. The second magnetic pole surface on the downstream side is more distant from the transport surface than the first magnetic pole surface on the upstream side, and a sloped surface arranged so that the distance from the transport surface gradually increases toward the transport direction connects between the first magnetic pole surface on the upstream side and the second magnetic pole surface on the downstream side.

The magnetically conductive member 21 is arranged at a location distant from the magnetization magnet 20 on the downstream side in the transport direction and the shape of its side surface is rectangular and longer in the vertical direction (in the Z-axis direction). The magnetically conductive member 21 is arranged so that the distance between its upper surface parallel to the transport surface and the transport surface is equivalent to a distance between a position more distant from the first magnetic pole surface on the upstream side of the magnetization magnet 20 and a position closer to the second magnetic pole surface on the downstream side of the magnetization magnet 20. The bottom surface of the magnetically conductive member 21 is located at the same vertical location as the bottom surface of the magnetization magnet 20.

The magnetization unit 3 is configured so that the magnetic field intensity of the magnetization magnetic field becomes maximum at the position P1, i.e., a position corresponding to an end of the first magnetic pole surface on the upstream side operation display unit in the transport direction. Specifically, by using the magnetization magnet 20 and the magnetically conductive member 21, the magnetic field intensity at the magnetizing position P1 on the transport path is set so that it becomes 1.5 times or more than the coercive force (3,000 Oe) of the high-coercive force magnetic material (4,500 G or more). The magnetization unit 3 is set so that the magnetic field intensity at the position P2 on the downstream side of the position P1 becomes 1.5 times or more of the coercive force (300 Oe) of the middle-coercive force magnetic material and 1 time or less (450 G to 3,000 G) than the coercive force of the high-coercive force magnetic material. In other words, the magnetization unit 3 is configured so that the magnetic field intensity of the first magnetic field region including the position P1 on the transport path and the magnetic field intensity of the second magnetic field region including the position P2 downstream of the position P1 in the transport direction becomes a specific magnetic field intensity.

In the magnetization unit 3, the magnetization magnet 20 and the magnetically conductive member 21 generate a magnetization magnetic field in a direction shown in FIG. 10B by curved broken line arrows. Specifically, the magnetization magnetic field is generated so that a direction 1201 of the magnetization magnetic field at the position P1 is within a range of angle between −100 degrees and −170 degrees and a direction 1202 of the magnetization magnetic field at the position P2 is within a range of angle between 100 degrees and 180 degrees. In other words, the magnetization unit 3 is configured so that the magnetic field direction of the first the magnetic field region including the position P1 on the transport path and the magnetic field direction of the second magnetic field region including the position P2 on the downstream side of the position P1 in the transport direction becomes a specific magnetic field direction. It is preferable that the magnetic field direction 1201 at the position P1 is close to −120 degrees and the magnetic field direction 1202 at the position P2 is close to 120 degrees, for example. In the following explanation, it is assumed that the magnetic field direction 1201 at the position P1 is −120 degrees and the magnetic field direction 1202 at the position P2 is 120 degrees.

In FIG. 10C, the magnitude of the magnetization magnetic field generated by the magnetization unit 3 is indicated by the length of broken line arrows and the direction of the magnetization magnetic field is indicated by the orientation of the broken line arrows. As explained above, in the magnetization unit 3, the magnetic field intensity of the magnetization magnetic field gradually weakens from the first magnetic pole surface on the upstream side in the transport direction of the magnetization magnet 20 toward the downstream side in the transport direction. The direction of the magnetization magnetic field gradually turns clockwise in the drawing from the angle of −120 degrees toward −180 degrees as one goes toward the downstream in the transport direction from the position of −120 degrees set at the magnetic field direction 1201 at the position P1. As one goes further downstream in the transport direction, the direction of the magnetization magnetic field gradually turns clockwise in the drawing from the position of −180 degrees (180 degrees) toward 120 degrees that is the magnetic field direction 1202 at the position P2.

As explained above, one of the characteristics of the present embodiment is such that the magnetization magnetic field generated by the magnetization unit 3 includes the first magnetic field region including the position P1 on the transport path and the second magnetic field region including the position P2 on the transport path that is downstream of the position P1 in the transport direction, and that the magnetic field intensity and the magnetic field direction are different between the first magnetic field region and the second magnetic field region. In the magnetization magnetic field generated by the magnetization magnet 20 and the magnetically conductive member 21 constituting the magnetization unit 3, the magnetic field intensity gradually weakens and the magnetic field direction gradually turns as one goes from the position P1 on the transport path toward the position P2. For example, the magnetic field direction 1201 at the position P1 is set at −120 degrees, the magnetic field intensity at the position P1 is set to 1.5 times or more than the coercive force of the high-coercive force magnetic material, the magnetic field direction 1202 at the position P2 is set at 120 degrees, and the magnetic field intensity at the position P2 is set to 1.5 times or more than the coercive force of the middle-coercive force magnetic material and 1 time or less than the coercive force of the high-coercive force magnetic material.

As a result, as shown in FIG. 10A, if the magnetic material included in the paper sheet 100 is the high-coercive force magnetic material, a magnetization direction 1501a of the high-coercive force magnetic material at the position P1 is in the same direction (about −120 degrees) as the magnetic field direction 1201 at the position P1 of the first magnetic field region. The paper sheet 100 is further transported in the transport direction 400, and because the magnetic field intensity of the magnetization magnetic field gradually weakens, the magnetized state of the high-coercive force magnetic material does not vary, and magnetization directions 1502a, 1503a, and 1504a at the positions P2 to P4, respectively, are in the same direction as the magnetization direction 1501a at the position P1.

If the magnetic material included in the paper sheet 100 is the middle-coercive force magnetic material, because the magnetic material is magnetized into the saturation magnetization state at the position P1 similarly to the case of the high-coercive force magnetic material, a magnetization direction 1501b is in the same direction (about −120 degrees) as the magnetic field direction 1201 of the first magnetic field region. However, because the coercive force of the middle-coercive force magnetic material is lower than that of the high-coercive force magnetic material, the middle-coercive force magnetic material is continuously influenced by the magnetization magnetic field while being transported in the transport direction 400. Accordingly, when the paper sheet 100 passes the position P2, a second magnetization direction 1502b of the middle-coercive force magnetic material is in the same direction (about 120 degrees) as the magnetic field direction 1202 of the second magnetic field region. As the paper sheet 100 is further transported, the paper sheet 100 is influenced by the bias magnetic field, and at the position P3, the magnetization direction of the paper sheet 100 becomes a magnetization direction 1503b, which is a direction reached by slightly turning from the second magnetization direction 1502b at the position P2 toward the direction 301 of the bias magnetic field at the position P3. Also at the position 24, the magnetization direction turns to a magnetization direction 1504b reached by slightly turning from the magnetization direction 1503b at the position P3 toward the direction 302 of the bias magnetic field at the position P4. However, because the magnetic field intensity of the bias magnetic field (450 G) is lower than the magnetic field intensity (300 Oe) necessary for magnetizing the coercive force of the middle-coercive force magnetic material into the saturation magnetization state, the final magnetic field direction of the middle-coercive force magnetic material becomes the magnetization direction 1504b that is a direction (about 120 degrees) between the second magnetization direction 1502b at the position P2 in the second magnetic field region and the direction 302 (between 30 degrees and 60 degrees) of the bias magnetic field at the position P4.

If the magnetic material included in the paper sheet 100 is the low-coercive force magnetic material, the magnetic material is magnetized into the saturation magnetization state at the position P1 similarly to the cases of other magnetic materials, and a magnetization direction 1501c (about −120 degrees) is in the same direction as the magnetic field direction 1201 in the first magnetic field region. However, because the coercive force of the low-coercive force magnetic material is low, the magnetic material is continuously influenced by the magnetization magnetic field while the paper sheet 100 is transported in the transport direction 400. Accordingly, similarly to the middle-coercive force magnetic material, a magnetization direction 1502c at the timing of passage over the position P2 is in the same direction (about 120 degrees) as the magnetic field direction 1202 in the second magnetic field region. As the paper sheet 100 is further transported, the paper sheet 100 is influenced by the bias magnetic field, and at the position P3, the magnetization direction becomes the same magnetization direction 1503c as the direction 301 of the bias magnetic field. Also at the position P4, the magnetization direction becomes the same magnetization direction 1504c as the direction 302 of the bias magnetic field. The magnetic field intensity of the bias magnetic field (450 G) is sufficiently higher than the coercive force (50 Oe) of the low-coercive force magnetic material, so that the low-coercive force magnetic material is magnetized into the saturation magnetization state at the respective positions. Accordingly, the magnetization directions of the low-coercive force magnetic material at the respective positions are in the same direction as the direction of the bias magnetic field at the respective positions.

As explained above, also in the present embodiment, similarly to the first embodiment, at the detection position P4 at which the detection is performed by the magnetic detection unit 2, the magnetization directions of the magnetic materials can be set according to the coercive force thereof. As explained above in the first embodiment, the type of the magnetic material can be determined based on the detection signal for the magnetic material that passes through the transport path.

Next, the reason why it is preferable if the magnetic field direction 1201 at the position P1 be about −120 degrees and the magnetic field direction 1202 be about 120 degrees will be explained. As shown in FIG. 10A, at the position P4 at which the magnetic material included in the paper sheet 100 is detected by the magnetic detection unit 2, the magnetization direction 1504a of the high-coercive force magnetic material is in the same direction as the magnetic field direction 1201 at the position P1 in the first magnetic field region, and the magnetization direction 1504b of the middle-coercive force magnetic material is a direction reached by slightly turning from the magnetic field direction 1202 at the position P2 in the second magnetic field region toward the direction 302 of the bias magnetic field.

Among FIG. 11A to FIG. 11H, FIG. 11A to FIG. 11D show the distribution of the magnetic fields around immediately below the magnetic material (around immediately below the magnetic material by a clearance of 0.5 mm) having been magnetized in magnetization directions 1507 to 1510, respectively, and FIG. 11E to FIG. 11H show the distribution of the magnetic field around immediately below the magnetic material (around immediately below the magnetization magnetic field by a clearance of 0.5 mm) having been magnetized in magnetization directions 1511 to 1514, respectively. Specifically, the magnetization direction 1507 shown in FIG. 11A is −180 degrees, the magnetization direction 1508 of FIG. 11B is −160 degrees, the magnetization direction 1509 of FIG. 11C is −120 degrees, and the magnetization direction 1510 of FIG. 11D is −90 degrees. A magnetization direction 1511 shown in FIG. 11E is 180 degrees, a magnetization direction 1512 of FIG. 11F is 160 degrees, a magnetization direction 1513 of FIG. 11G is 120 degrees, and a magnetization direction 1514 of FIG. 11H is 90 degrees. If the magnetic field direction 1201 at the position P1 is set at −180 degrees, −160 degrees, −120 degrees, and −90 degrees, the magnetic field distribution of the high-coercive force magnetic material at the position P4 will be as shown in FIG. 11A to FIG. 11D, and if the magnetic field direction 1202 at the position P2 is set at 180 degrees, 160 degrees, 120 degrees, and 90 degrees, the magnetic field distribution of the middle-coercive force magnetic material at the position P4 will be substantially the same as the distribution shown in FIG. 11E to FIG. 11H. The magnetic field distribution is detected by the magnetic detection unit 2.

The magnetic signal is detected in the magnetic detection unit 2 so that the shapes of the magnetic field distributions shown in FIG. 11A to FIG. 11D are followed from left to right. As shown in FIG. 11B, the high-coercive force magnetic material having been magnetized into the magnetization direction 1508 oriented toward −160 degrees, an overshoot magnetic signal corresponding to the magnetic field distribution on the positive side is detected after a magnetic signal corresponding to the magnetic field distribution on the negative side is detected. In the overshoot magnetic signal, the magnetic field distribution shown in FIG. 11C corresponding to the magnetic material having been magnetized in the magnetization direction 1509 of −120 degrees is smaller than the magnetic field distribution shown in FIG. 11B corresponding to the magnetic material having been magnetized in the magnetization direction 1508 of −160 degrees, and thus it is more preferable that the magnetization direction is −120 degrees rather than −160 degrees.

Similarly, in the magnetic detection unit 2, the magnetic signal is detected so as to follow the shape of the magnetic field distribution shown in FIG. 11E to FIG. 11H from right to left. As shown in FIG. 11F, in the middle-coercive force magnetic material having been magnetized in the magnetization direction 1512 of 160 degrees, an overshoot magnetic signal corresponding to the magnetic field distribution on the negative side is detected after a magnetic signal corresponding to the magnetic field distribution on the positive side is detected. In the overshoot magnetic signal, the magnetic field distribution shown in FIG. 11G corresponding to the magnetic material having been magnetized in the magnetization direction 1513 of 120 degrees is smaller than the magnetic field distribution shown in FIG. 11F corresponding to the magnetic material having been magnetized in the magnetization direction 1512 of 160 degrees, and thus it is more preferable that the magnetization direction is about 120 degrees rather than 160 degrees.

If the overshoot only is considered, FIG. 11D in which the magnetization direction 1510 is −90 degrees is more preferable than FIG. 11C in which the magnetization direction 1509 is −120 degrees if the magnetic material is the high-coercive force magnetic material. Similarly, FIG. 11H in which the magnetization direction 1513 is 120 degrees is more preferable than FIG. 11G in which the magnetization direction 1513 is 120 degrees if the magnetic material is the middle-coercive force magnetic material. However, if the magnetic field direction 1201 of the first the magnetic field region is set at −90 degrees and the magnetic field direction 1202 of the second magnetic field region is set at 90 degrees, the detected waveform becomes a waveform obtained by adding the waveform of the magnetic field distributions shown in FIG. 11D and FIG. 11H if a laminated magnetic material obtained by laminating a high-coercive force magnetic material and a middle-coercive force magnetic material is to be detected, and thus the magnetic field distributions are set off, and therefore the laminated magnetic material cannot be detected. Accordingly, in the present embodiment, in order to determine the high-coercive force magnetic material, the middle-coercive force magnetic material, and the laminated magnetic material including the high-coercive force magnetic material and the middle-coercive force magnetic material, respectively, based on the detection signal at the position P4, the magnetic field direction 1201 at the position P1 is set at about −120 degrees and the magnetic field direction 1202 at the position P2 is set at about 120 degrees.

As explained above in the first embodiment with reference to FIG. 6, also in the present embodiment, the direction of the magnetization magnetic field and the direction of the bias magnetic field are not limited to those shown in FIG. 10. FIG. 12 is a view that illustrates the configuration shown in FIG. 10 similarly to FIG. 6A. As is clear from the relationship between FIG. 6A and FIG. 6B to FIG. 6D, even if the location of arrangement and the direction of the magnetization unit 3 and the magnetic detection unit 2 shown in FIG. 12 are changed so as to correspond to those in FIG. 6B to FIG. 6D, the type of the magnetic materials can be determined by magnetizing the magnetic materials in mutually different directions according to their coercive force.

As explained above in the first embodiment with reference to FIG. 1 and FIG. 8, the relationship among the directions 1201 and 1202 of the magnetization magnetic field, the direction 302 of the bias magnetic field and the transport direction 400 at the position P4 at which the magnetism is detected are not limited to those in the case of the forward-direction transport shown in FIG. 10. That is, those for the reverse-direction transport can be used.

Figure 13A:
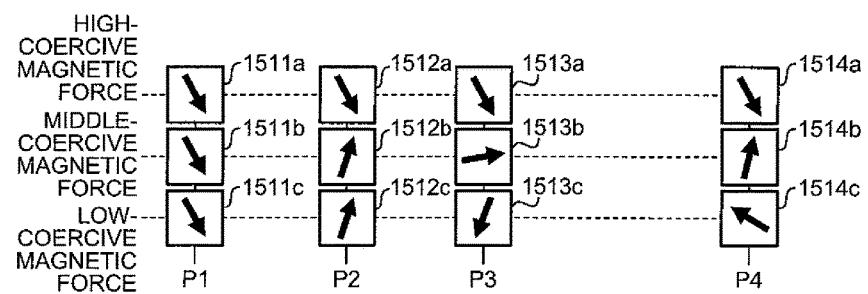
FIGS. 13A and 13B are views that show an example of a magnetic property determination method with reverse-direction transporting according to the second embodiment.
Figure 13B:
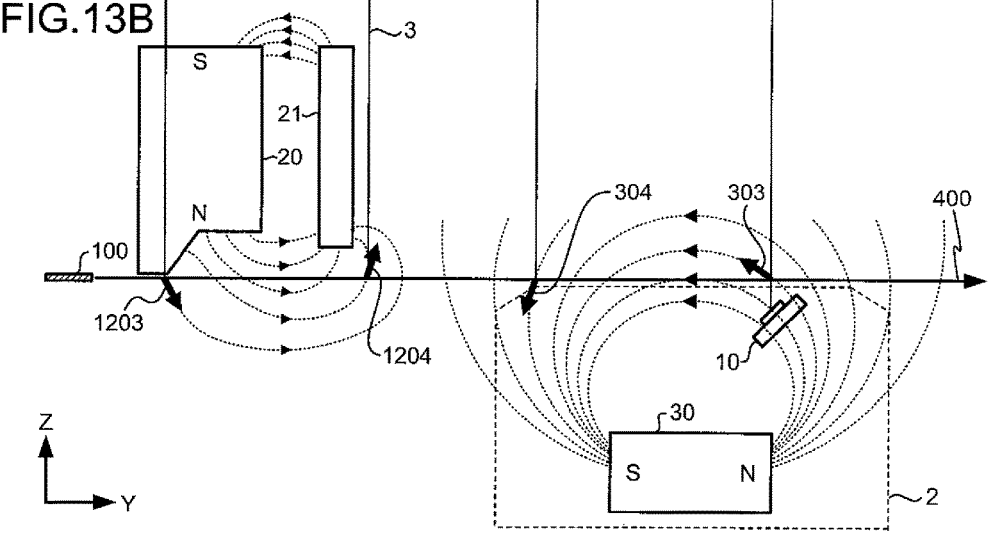

FIG. 13A and FIG. 13B are schematic diagrams that show the magnetic property determination method in the case of the reverse transport direction. FIG. 13B shows an outline of the magnetic property determination apparatus 1, and FIG. 13A shows the magnetized state of the 3 types of magnetic materials with mutually different coercive forces. The configuration of the magnetic property determination apparatus 1 shown in FIG. 13B is different from the magnetic property determination apparatus 1 shown in FIG. 10(B) in that in the magnetic property determination apparatus 1 shown in FIG. 13B the magnetization unit 3 is arranged above the transport path and vertically reversed around the Y-axis and that the magnetic detection unit 2 is arranged and laterally reversed around the Z-axis. In the magnetic property determination apparatus 1 shown in FIG. 13B, the directions 1203 and 1204 of the magnetization magnetic field and the direction 303 of the bias magnetic field are vertically reversed around the Z-axis from the magnetic field directions 1201 and 1202 and the magnetic field direction 302 shown in FIG. 10B.

If the magnetic material included in the paper sheet 100 is the high-coercive force magnetic material, when the paper sheet 100 is transported in the transport direction 400, because the magnetic field intensity of the magnetization magnetic field (4,500 G) is very high, the magnetic material is magnetized into the saturation magnetization state or into a magnetized state close to the saturation magnetization state when the paper sheet 100 passes the position P1 shown in FIG. 13B. In this process, a magnetization direction 1511a of the high-coercive force magnetic material is in the same direction (about −60 degrees) as the magnetic field direction 1203 at the position P1. When the paper sheet 100 is transported further in the transport direction 400, no such magnetic field exists that is intense enough to change the magnetized state of the high-coercive force magnetic material thereafter, and thus subsequent magnetization directions 1512a, 1513a, and 1514a remain to be in the same direction as the magnetization direction 1511a at the timing of the magnetization, i.e., the direction 1203 of the magnetization magnetic field.

If the magnetic material included in the paper sheet 100 is the middle-coercive force magnetic material, the magnetic material is magnetized into the saturation magnetization state at the position P1. However, because the coercive force of the middle-coercive force magnetic material is low compared with the high-coercive force magnetic material, the magnetic material is continuously influenced by the magnetization magnetic field and the bias magnetic field while the paper sheet 100 is transported in the transport direction 400, and thus the magnetization direction 1512b at the position P2 and the magnetization direction 1513b at the position P3 vary. Specifically, the magnetization direction 1512b at the position P2 is the magnetic field direction 1204 at the position P2 (about 60 degrees), and the magnetization direction 1513b at the position P3 is a direction between the magnetic field direction 1204 at the position P2 and the direction 304 of the bias magnetic field at the position P3. A final magnetization direction 1514b is a direction between the magnetization direction 1513b at the position P3 and the direction 303 of the bias magnetic field at the subsequent position P4. Because the magnetic field direction 303 at the position P4 and the magnetization direction 1513b at the position P3 are opposite, the coercive force of the middle-coercive force magnetic material is weakened, and thus the amplitude of the detection waveform of the middle-coercive force magnetic material is lower than that in the forward-direction transport.

If the magnetic material included in the paper sheet 100 is the low-coercive force magnetic material, because the coercive force of the low-coercive force magnetic material is low, the magnetic material is continuously influenced by the magnetization magnetic field and the bias magnetic field while the paper sheet 100 is transported in the transport direction 400, and thus magnetization directions 1511c to 1514c at the respective positions P1 to P4 are the same as the magnetic field directions 1203, 1204, 304, and 303 at the position.

Accordingly, also in the case of reverse-direction transport, similarly to the case of the forward-direction transport shown in FIG. 10, all of the magnetization direction 1514a of the high-coercive force magnetic material, the magnetization direction 1514b of the middle-coercive force magnetic material, and the magnetization direction 1514c of the low-coercive force magnetic material can be set in the mutually different directions. Accordingly, detection signals having different waveforms can be obtained among the high-coercive force magnetic material, the middle-coercive force magnetic material, the low-coercive force magnetic material, and the laminated magnetic materials.

Figure 14:
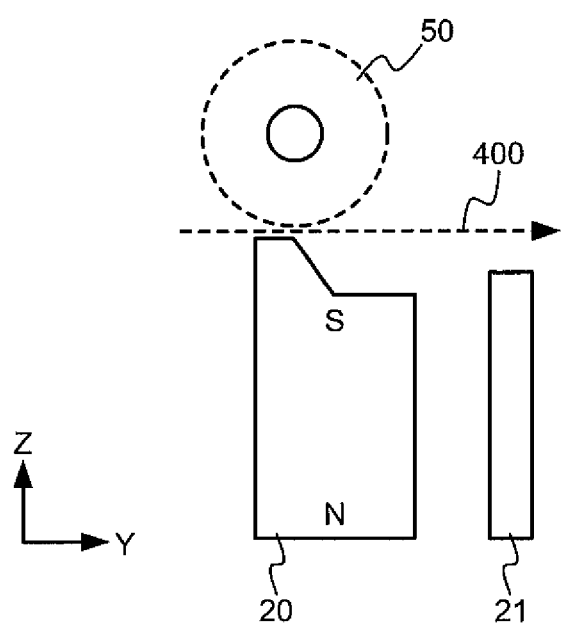
FIG. 14 is a view that shows an example of a configuration for regulating a passing position of a paper sheet on a transport path.

As shown in FIG. 10, FIG. 12, and FIG. 13, if the magnetization unit 3 is arranged on one side of the transport path, it is preferable that the positions that the paper sheet 100 passes be regulated to prevent the paper sheet 100 including the magnetic material from jumping from the transport path and passing at positions distant from the magnetization unit 3. FIG. 14 is a view that shows an example of a configuration for regulating the position of passage of the paper sheet 100 on the transport path. A brush roller 50 that is rotatably supported is arranged at an opposite position of the magnetization magnet 20 across the transport path. When the paper sheet 100 is transported in the transport direction 400 the brush roller 50 is operative to press the paper sheet 100 toward the magnetization magnet 20. With this configuration, the positions that the paper sheet 100 passes can be regulated so that the paper sheet 100 would not move too far from the first magnetic pole surface of the magnetization magnet 20 parallel to the transport surface on the upstream side in the transport direction.

If the magnetic field direction 1201 at the position P1 and the magnetic field direction 1202 at the position P2 can be realized, the shapes of the magnetization magnet 20 and the magnetically conductive member 21 are not limited to those shown in FIG. 10. FIG. 15A to FIG. 15D are views that an example of the shape of the side surface of the magnetization magnet 20 and the magnetically conductive member 21. In FIG. 15A to FIG. 15D, the shape of the side surfaces of the magnetization magnet 20 and the magnetically conductive member 21 are shown in such a manner that the transport direction 400 of the paper sheet 100 is the right portion of the drawing in the lateral direction.

Figure 15A:
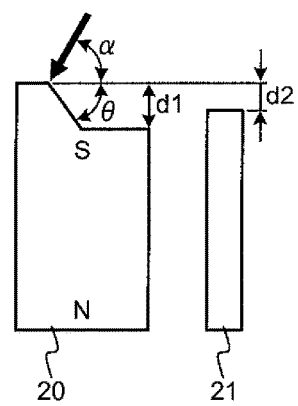
FIGS. 15A, 15B, 15C and 15D are views that show an example of the shape of a side surface of a magnetization magnet and the magnetically conductive member.

In order to set the angle α of the magnetic field direction of the first the magnetic field region shown in FIG. 15A to about −120 degrees, a sloped surface that connects the first magnetic pole surface parallel to the transport surface and on the upstream side in the transport direction with the second magnetic pole surface parallel to the transport surface and on the downstream side can be formed so that an angle θ against the transport surface be between 15 degrees and 85 degrees. It is sufficient that a distance d1 between the transport surface and the second magnetic pole surface of the magnetization magnet 20 is about 1 mm, and a distance d2 between the transport surface and a top surface of the magnetically conductive member 21 is about 0.5 mm to 1 mm.

Figure 15B:
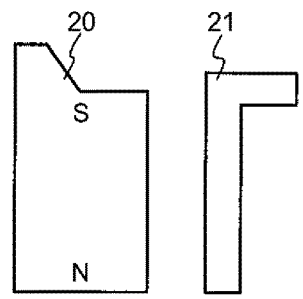
Figure 15C:
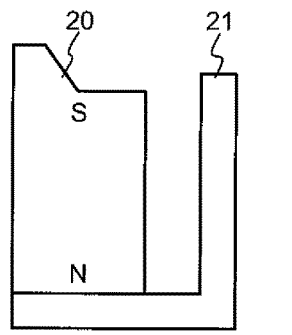
Figure 15D:
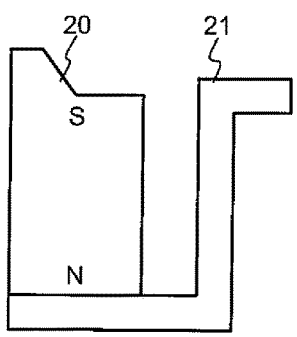

The shape of the side surface of the magnetically conductive member 21 can be a shape obtained by rotating the L-like shape as shown in FIG. 15B, a reversed L-like shape arranged that contacts the bottom surface of the magnetization magnet 20, or an S-like shape that contacts the bottom surface of the magnetization magnet 20 shown in FIG. 15D.

Figure 16A:
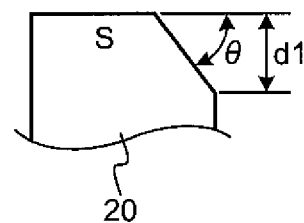
Figure 16B:
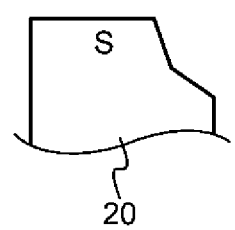
Figure 16C:
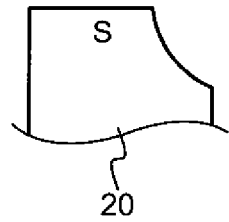
Figure 16D:
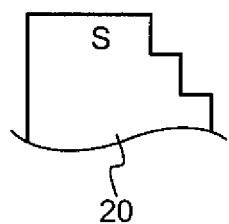

FIG. 16A to FIG. 16D are views show another example of the shape of the side surface of the magnetization magnet 20. Also in FIG. 16A to FIG. 16D, a part of the upper portion of the shape of the side surface of the magnetization magnet 20 is shown so that the transport direction 400 of the paper sheet 100 is in the right portion of the drawing in the lateral direction. If the magnetic field intensity takes its maximum value at a point on the top surface of the magnetization magnet 20 corresponding to the position P1 and if the magnetic field direction can be gradually varied while the magnetic field intensity of the magnetization magnetic field is reduced from the point toward the position P2 corresponding to the magnetically conductive member 21 as shown in FIG. 10O, then the shape of the side surface of the magnetization magnet 20 on the side of its top surface can take a chamfered shape shown in FIG. 16A to 16D. Specifically, as shown in FIG. 16A, the side surface shape can be a shape in which a part thereof on the side of the downstream side in the transport direction on the side of the top surface of the magnetization magnet 20 (the upper right portion in the drawing) so as to correspond to the angle θ and the distance d1 shown in FIG. 15A. In alternative configurations, the side surface shape can be a side surface shape in which the cutoff portion is bent as shown in FIG. 16B, a side surface shape in which the cutoff portion is a curved surface as shown in FIG. 16C, a side surface shape in which the cutoff portion has a step-like shape as shown in FIG. 16D, or the like.

Figure 17A:
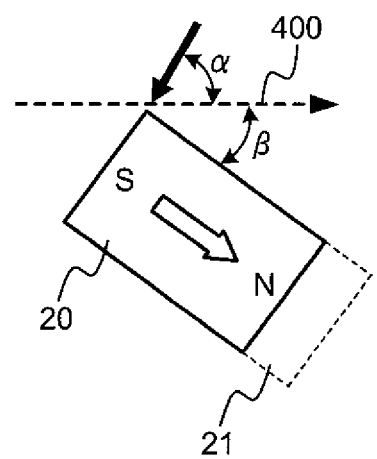
FIG. 17A and FIG. 17B are views that show an example of adjustment of the direction of the magnetization magnetic field by changing the angle of arrangement of the magnetization magnet and the angle of magnetization of a magnetization magnet 20.
Figure 17B:
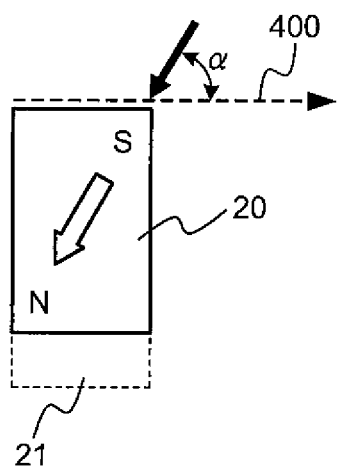

In a yet alternative configuration, the magnetic field directions 1201 and 1202 shown in FIG. 10 can be implemented by using the magnetization magnet 20 having a rectangular side surface shape. FIG. 17A and FIG. 17B are views illustrate examples in which the direction of the magnetization magnetic field is adjusted based on the angle of arrangement of the magnetization magnet 20 or the magnetization angle of the magnetization magnet 20. In FIG. 17A and FIG. 17B, a white blank arrow indicates the magnetization direction of magnetization the magnet 20 itself. In an alternative configuration, the magnetization magnet 20 with a magnetization direction parallel to one side of the rectangular side surface shape can be inclined and the magnetization magnet 20 can be arranged by adjusting an angle β against the transport direction 400 so that the angle α between the direction of the magnetization magnetic field at an end on the downstream side in the transport direction on the side of the top surface and the transport direction 400 become −120 degrees. In a yet another configuration, the magnetic field direction of the magnetization magnet 20 can be adjusted so that the angle α between the direction of the magnetization magnetic field at an end on the downstream side in the transport direction on the side of the top surface and the transport direction 400 becomes −120 degrees when the magnetization magnet 20 of which the shape of the side surface is a rectangular shape is arranged so that one side of the rectangular shape is in parallel to the transport direction 400 as shown in FIG. 17B. In yet another configurations, a magnetic material having been cut to have a rectangular shape may be magnetized so that the magnetic field direction thereof is the magnetic field direction shown in FIG. 17B by a white blank arrow and the magnetic material magnetized in this manner is used as the magnetization magnet 20, or the magnetization magnet 20 can be cut off from a magnet having been magnetized in a specific direction so that the magnetic field direction thereof becomes the magnetic field direction shown in FIG. 17B by a white blank arrow and the magnetization magnet 20 prepared in this manner may be used. The magnetization magnet 20 only can be used, or the magnetically conductive member 21 can be arranged on the side of one end of the magnetization magnet 20 in the manners shown in FIG. 17A and FIG. 17B by broken arrow lines.

As explained above, according to the present embodiment, by appropriately setting the magnetic field intensity of the magnetization magnet 20, the shape of the magnetization magnet 20, the shape of the magnetically conductive member 21, the relationship between the arrangement location of the magnetization magnet 20 and the arrangement location of the magnetically conductive member 21, and the like so that the magnetic field directions 1201 and 1202 take a specific angle in the first magnetic field region including the position P1 on the transport path and the second magnetic field region including the position P2 on the transport path that is downstream of the position P1 and so that the magnetic field intensity of the first magnetic field region and the magnetic field intensity of the second magnetic field region become an appropriate magnetic field intensity, the magnetization directions of the respective magnetic materials can be set to mutually different directions at the position P4 at which magnetism is detected by the magnetic detection unit 2 according to the coercive force. Therefore, the type of the magnetic materials with mutually different coercive forces can be determined based on the characteristics of the detection signal obtained when the magnetism is detected.

INDUSTRIAL APPLICABILITY

As explained above, the present invention is useful in detecting and determining plural magnetic materials with mutually different coercive forces by using a small-size magnetic property determination apparatus.

EXPLANATION OF REFERENCE NUMERALS

1 Magnetic property detection apparatus
2 Magnetic detection unit
3 Magnetization unit
10 Magnetic unit
20 Magnetization magnet
21 Magnetically conductive member
30 Bias magnet
50 Brush roller
100 Paper sheet

The invention claimed is:

1. A magnetic property determination apparatus that detects a magnetic material included in a paper sheet transported through a transport path and determines a type among three types of magnetic materials, a first magnetic material having a coercive force, a second magnetic material having a coercive force lower than that of the first magnetic material, and a third magnetic material having a coercive force lower than that of the second magnetic material, the apparatus comprising:
a magnetic detection unit that generates on the transport path a bias magnetic field having a magnetic field direction inclined to a transport surface of the paper sheet by a predetermined angle and detects the magnetic charge of the magnetic materials by detecting variation of the bias magnetic field; and
a magnetization unit that is arranged upstream of the magnetic detection unit in a transport direction and magnetizes the magnetic material by generating on the transport path a magnetization magnetic field having a magnetic field direction oriented in a direction different from the direction of the bias magnetic field,
wherein at a position at which the magnetic detection unit detects the magnetic material transported in the magnetization magnetic field and the bias magnetic field, each of the three types of magnetic materials is in a state in which the three types of magnetic materials are magnetized in mutually different magnetization directions according to coercive force thereof.

2. The magnetic property determination apparatus according to claim 1, wherein
magnetic field intensity of the magnetization magnetic field is set to magnetic field intensity for magnetizing the first magnetic material into a saturation magnetization state, and
the magnetic field intensity of the bias magnetic field is set to magnetic field intensity for magnetizing the third magnetic material into the saturation magnetization state and for not magnetizing other magnetic materials into the saturation magnetization state.

3. The magnetic property determination apparatus according to claim 2, wherein
the magnetic field intensity of the magnetization magnetic field is set to 1.5 times or more than the coercive force of the first magnetic material, and
the magnetic field intensity of the bias magnetic field is set to 2 times or less than the coercive force of the second magnetic material.

4. The magnetic property determination apparatus according to claim 1, wherein
the transport direction is taken as 0 degrees, and
the direction of the bias magnetic field is set to a range between 30 degrees and 60 degrees or between 120 degrees and 150 degrees, and the direction of the magnetization magnetic field is set within a range excluding a range between 80 degrees and 100 degrees, or
the direction of the bias magnetic field is set to a range between −30 degrees and −60 degrees or between −120 degrees and −150 degrees and the direction of the magnetization magnetic field is set within a range excluding a range between 80 degrees and 100 degrees.

5. The magnetic property determination apparatus according to claim 1, wherein
the transport direction is taken as 0 degrees, and
a combination of the direction of the bias magnetic field and the direction of the magnetization magnetic field is set to any one of a range between 30 degrees and 60 degrees and between −100 degrees and −170 degrees, between 120 degrees and 150 degrees and between −10 and −80 degrees, between −30 degrees and −60 degrees and between −100 and −170 degrees, and between −120 degrees and −150 degrees or between −10 degrees and −80 degrees.

6. The magnetic property determination apparatus according to claim 1, wherein the magnetic detection unit determines the coercive force of the magnetic material based on the shape of a waveform of a detection signal obtained when the magnetic material is detected.

7. The magnetic property determination apparatus according to claim 6, wherein the waveform of the detection signal of the third magnetic material is substantially symmetric in relation to a peak position.

8. The magnetic property determination apparatus according to claim 6, wherein
an output of a signal obtained when detecting the third magnetic material is taken as a positive output,
the detection signal of the second magnetic material has a positive peak value and a negative peak value, a waveform of the detection signal is asymmetric in relation to a peak position,
a ratio of a positive output is higher than a ratio of a negative output in the detection signal, and
the detection signal of the first magnetic material has a positive peak value and a negative peak value, a waveform of the detection signal is asymmetric in relation to a peak position, and the ratio of the negative output is higher than the ratio of the positive output in the detection signal.

9. The magnetic property determination apparatus according to claim 6, wherein
the detection signal of a laminated magnetic material including the second magnetic material and the first magnetic material, or including the third magnetic material and the first magnetic material has a positive peak value and a negative peak value, and
the detection signal has a waveform obtained by adding the detection signal of the second magnetic material and the detection signal of the first magnetic material.

10. A magnetic property determination apparatus that detects a magnetic material included in a paper sheet transported through a transport path and determines a type among three types of magnetic materials, a first magnetic material having a coercive force, a second magnetic material having a coercive force lower than that of the first magnetic material, and a third magnetic material having a coercive force lower than that of the second magnetic material, the apparatus comprising:
a magnetic detection unit that generates on the transport path a bias magnetic field having a magnetic field direction inclined to a transport surface of the paper sheet by a predetermined angle and detects the magnetic charge of the magnetic materials by detecting variation of the bias magnetic field; and
a magnetization unit that is arranged upstream of the magnetic detection unit in a transport direction and magnetizes the magnetic materials by generating on the transport path a magnetization magnetic field,
wherein the magnetization magnetic field includes a first magnetic field region on the transport path and a second magnetic field region on the transport path downstream of the first magnetic field region,
wherein magnetic field intensity of the first magnetic field region is set to magnetic field intensity for magnetizing the first magnetic material into a saturation magnetization state or to a state close to the saturation magnetization state, and magnetic field intensity of the second magnetic field region is set to magnetic field intensity for magnetizing the second magnetic material into the saturation magnetization state or to a state close to the saturation magnetization state, and the magnetic field direction of the first magnetic field region and the magnetic field direction of the second magnetic field region are set to mutually different directions,
wherein at a position at which the magnetic detection unit detects the magnetism, the magnetic materials are in a state in which the magnetic materials are magnetized by the magnetization magnetic field and the bias magnetic field in mutually different magnetization directions according to the coercive force thereof.

11. The magnetic property determination apparatus according to claim 10, wherein
for the first the magnetic field region, the magnetic field direction is set within a range between −100 degrees and −170 degrees in relation to the transport direction that is taken as 0 degrees and the magnetic field intensity is set to 1.5 times or more than the coercive force of the first magnetic material.

12. The magnetic property determination apparatus according to claim 10, wherein
for the second magnetic field region, the magnetic field direction is set within a range between 100 degrees and 180 degrees in relation to the transport direction that is taken as 0 degrees and the magnetic field intensity is set to 1.5 times or more than the coercive force of the second magnetic material and 1 time or less than the coercive force of the first magnetic material.

13. The magnetic property determination apparatus according to claim 10 wherein the magnetization unit includes a magnetization magnet and a magnetically conductive member arranged downstream of the magnetization magnet in the transport direction.

14. The magnetic property determination apparatus according to claim 13 , wherein
the magnetization magnet includes one magnetic pole surface that is substantially parallel to a transport surface, which is arranged on a side of a top surface opposed to the transport path, and another magnetic pole surface that is more distant from the transport surface than the one magnetic pole surface, which is arranged downstream of the one magnetic pole surface in the transport direction.

15. The magnetic property determination apparatus according to claim 13, wherein the magnetization magnet includes a chamfered region arranged downstream on the top surface opposed to the transport direction in the transport direction.

16. A magnetic property determination method of detecting a magnetic property of magnetic material included in a paper sheet transported through a transport path and determining a type among three types of magnetic materials, a first magnetic material having a coercive force, a second magnetic material having a coercive force lower than that of the first magnetic material, and a third magnetic material having a coercive force lower than that of the second magnetic material, the method comprising:

generating on the transport path a bias magnetic field having a magnetic field direction inclined to a transport surface of the paper sheet by a predetermined angle and detecting the magnetic charge of the magnetic material by detecting variation of the bias magnetic field; and magnetizing the magnetic material by generating on the transport path a magnetization magnetic field having a magnetic field direction oriented in a direction different from the direction of the bias magnetic field, the magnetization field being on an upstream side of a position at which the magnetic charge is detected at the detecting, wherein when the magnetic charge is detected at the detecting, each of the three types of magnetic materials is in a state in which the three types of magnetic materials are magnetized by the magnetization magnetic field and the bias magnetic field in mutually different magnetization directions according to the coercive force thereof.

17. The magnetic property determination method according to claim 16 wherein the magnetization magnetic field includes a first magnetic field region on the transport path and a second magnetic field region on the transport path downstream of the first magnetic field region, wherein magnetic field intensity of the first magnetic field region is set to magnetic field intensity for magnetizing the first magnetic material into a saturation magnetization state or to a state close to the saturation magnetization state, and magnetic field intensity of the second magnetic field region is set to magnetic field intensity for magnetizing the second magnetic material into the saturation magnetization state or to a state close to the saturation magnetization state, and the magnetic field direction of the first magnetic field region and the magnetic field direction of the second magnetic field region are set to mutually different directions.

\* \* \* \* \*